United States Patent
Takemoto et al.

(10) Patent No.: US 8,329,377 B2
(45) Date of Patent: Dec. 11, 2012

(54) IMIDE COMPOUND AND CHEMICALLY AMPLIFIED RESIST COMPOSITION CONTAINING THE SAME

(75) Inventors: Ichiki Takemoto, Kawanishi (JP); Tatsuro Masuyama, Toyonaka (JP); Takashi Hiraoka, Hannan (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 566 days.

(21) Appl. No.: 12/506,942

(22) Filed: Jul. 21, 2009

(65) Prior Publication Data

US 2010/0028807 A1  Feb. 4, 2010

(30) Foreign Application Priority Data

Jul. 30, 2008  (JP) .................. 2008-195969

(51) Int. Cl.
 G03F 7/004 (2006.01)
 C07D 207/00 (2006.01)
 C07D 209/00 (2006.01)
 C07D 221/14 (2006.01)
 C07D 295/00 (2006.01)
 C08F 226/06 (2006.01)

(52) U.S. Cl. ............. 430/270.1; 430/907; 430/910; 430/920; 526/243; 526/248; 526/260; 526/265; 546/98; 548/437; 548/441; 548/450; 548/528; 548/529

(58) Field of Classification Search ........... 430/270.1, 430/907, 910, 920; 526/243, 248, 259, 260, 526/265; 546/98; 548/441, 450, 528, 529
See application file for complete search history.

(56) References Cited

U.S. PATENT DOCUMENTS 4,258,121 A * 3/1981 Kojima .................. 430/281.1
7,410,746 B2 * 8/2008 Sakayori ................ 430/270.1

FOREIGN PATENT DOCUMENTS

JP  2007-072214  3/2007
JP  2007072214 A  3/2007

\* cited by examiner

*Primary Examiner* — John Chu
(74) *Attorney, Agent, or Firm* — Hogan Lovells US LLP

(57) ABSTRACT

An imide compound represented by the formula (I):

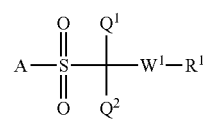

wherein $R^1$ represents a C1-C20 aliphatic hydrocarbon group etc., $W^1$ represents —CO—O— etc., $Q^1$ and $Q^2$ each independently represent a fluorine atom etc., and A represents a group represented by the formula (I-1):

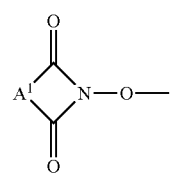

wherein $A^1$ represents —$CH_2$—$CH_2$— etc., and a chemically amplified resist composition containing the same.

13 Claims, No Drawings

IMIDE COMPOUND AND CHEMICALLY AMPLIFIED RESIST COMPOSITION CONTAINING THE SAME

This nonprovisional application claims priority under 35 U.S.C. §119(a) on Patent Application No. 2008-195969 filed in JAPAN on Jul. 30, 2008, the entire contents of which are hereby incorporated by reference.

FIELD OF THE INVENTION

The present invention relates to an imide compound and a chemically amplified resist composition containing the same.

BACKGROUND OF THE INVENTION

JP 2007-72214 A1 discloses a compound represented by the following formula, which is used as an acid generator.

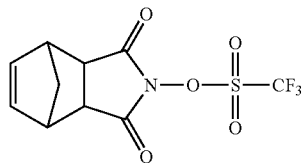

SUMMARY OF THE INVENTION

An object of the present invention is to provide a novel imide compound and a chemically amplified resist composition containing the same.

The present invention relates to the followings:

<1> An imide compound represented by the formula (I):

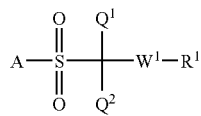

wherein $R^1$ represents a C1-C20 aliphatic hydrocarbon group, a C5-C10 aryl group or a C6-C20 aralkyl group, and the C1-C20 aliphatic hydrocarbon group, the C5-C10 aryl group and the C6-C20 aralkyl group may have one or more substituents and one or more heteroatoms, $W^1$ represents —CO—O—, —O—CO—, —CO$_2$O—, —O—CO$_2$—, —CH$_2$O—CO— or —CO—OCH$_2$—, $Q^1$ and $Q^2$ each independently represent a hydrogen atom, a fluorine atom, a C1-C6 alkyl group or a C1-C6 perfluoroalkyl group, and A represents a group represented by the formula (I-1):

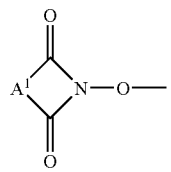

wherein $A^1$ represents —CH$_2$—CH$_2$—, —CH$_2$—CH$_2$—CH$_2$—, —CH═CH— or —CH═CH—CH$_2$—, in which one or more hydrogen atoms may be substituted with a C1-C6 aliphatic hydrocarbon group, a C3-C12 alicyclic hydrocarbon group or a C6-C10 aromatic hydrocarbon group, and the neighboring substituents may be bonded each other to form a ring, and the C1-C6 aliphatic hydrocarbon group, the C3-C12 alicyclic hydrocarbon group and the C6-C10 aromatic hydrocarbon group may have one or more substituents and one or more heteroatoms;

<2> The imide compound according to <1>, wherein $Q^1$ and $Q^2$ each independently represent a fluorine atom or a trifluoromethyl group;

<3> The imide compound according to <1>, wherein $Q^1$ and $Q^2$ are fluorine atoms;

<4> The imide compound according to any one of <1> to <3>, wherein $R^1$ is a C1-C20 alkyl group substituted with an acryloyloxy group or a methacryloyloxy group and the C1-C20 alkyl group may have one or more substituents and one or more heteroatoms;

<5> The imide compound according to any one of <1> to <3>, wherein $R^1$ is a C3-C20 alicyclic hydrocarbon group which may have one or more substituents and one or more heteroatoms;

<6> The imide compound according to any one of <1> to <5>, wherein the compound represented by the formula (I) is a compound represented by the formula (III), (IV), (V), (VI) or (VII):

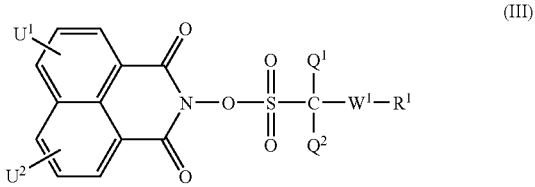

(III)

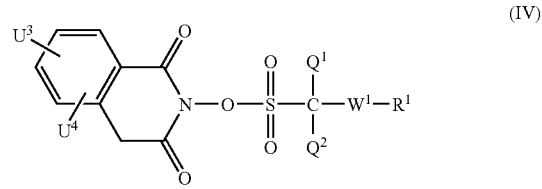

(IV)

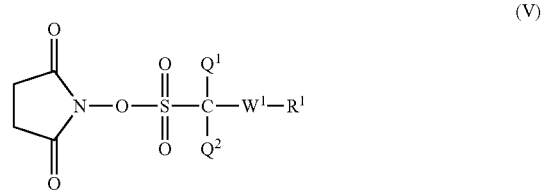

(V)

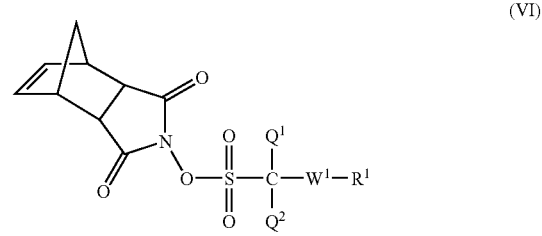

(VI)

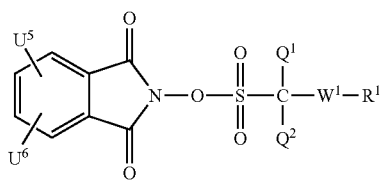
(VII)

wherein U¹ to U⁶ each independently represent a hydrogen atom, a C1-C4 hydrocarbon group or a C1-C4 alkoxy group, and R¹, W¹, Q¹ and Q² are the same meanings as defined above;

<7> A polymer comprising a structural unit derived from an imide compound according to <4>;

<8> The polymer according to <7>, wherein the polymer contains a structural unit having an acid-labile group in addition to the structural unit derived from an imide compound according to <4>;

<9> A chemically amplified resist composition comprising a resin and an imide compound according to any one of <1> to <6>;

<10> A chemically amplified resist composition comprising a resin and a polymer according to <7> or <8>;

<11> The chemically amplified resist composition according to <9> or <10>, wherein the resin is a resin comprising a structural unit having an acid-labile group and being insoluble or poorly soluble in an aqueous alkali solution but becoming soluble in an aqueous alkali solution by the action of an acid;

<12> The chemically amplified resist composition according to any one of <9> to <11>, wherein the resin further contains the other acid generator;

<13> A process for producing an imide compound represented by the formula (I):

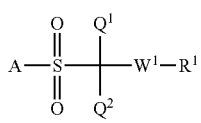
(I)

wherein R¹ represents a C1-C20 aliphatic hydrocarbon group, a C5-C10 aryl group or a C6-C20 aralkyl group, and the C1-C20 aliphatic hydrocarbon group, the C5-C10 aryl group and the C6-C20 aralkyl group may have one or more substituents and one or more heteroatoms,
W¹ represents —CO—O—, —O—CO—, —CH₂O—, —O—CH₂—, —CH₂O—CO— or —CO—OCH₂—,
Q¹ and Q² each independently represent a hydrogen atom, a fluorine atom, a C1-C6 alkyl group or a C1-C6 perfluoroalkyl group, and A represents a group represented by the formula (I-1):

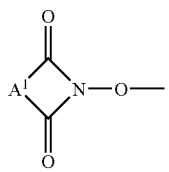
(I-1)

wherein A¹ represents —CH₂—CH₂—, —CH₂—CH₂—CH₂—, —CH=CH— or —CH=CH—CH₂—, in which one or more hydrogen atoms may be substituted with a C1-C6 aliphatic hydrocarbon group, a C3-C12 alicyclic hydrocarbon group or a C6-C10 aromatic hydrocarbon group, and the neighboring substituents may be bonded each other to form a ring, and the C1-C6 aliphatic hydrocarbon group, the C3-C12 alicyclic hydrocarbon group and the C6-C10 aromatic hydrocarbon group may have one or more substituents and one or more heteroatoms, which comprises reacting a compound represented by the formula (VIII):

A-H (VIII)

wherein A is the same as defined above, with a compound represented by the formula (IX):

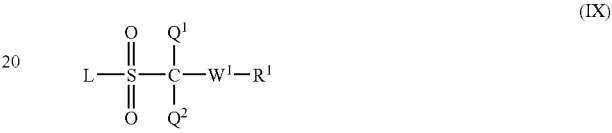
(IX)

wherein R¹, W¹, Q¹ and Q² are the same meanings as defined above, and L represents a halogen atom, in the presence of a base.

DESCRIPTION OF PREFERRED EMBODIMENTS

The imide compound represented by the formula (I):

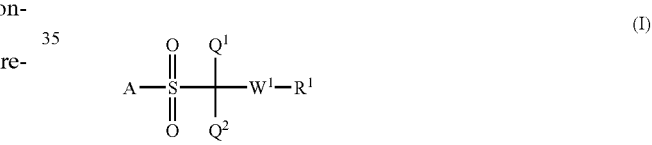
(I)

(hereinafter, simply referred to as imide (I)) is a novel compound. In the formula (I), R¹ represents a C1-C20 aliphatic hydrocarbon group, a C5-C10 aryl group or a C6-C20 aralkyl group.

The C1-C20 aliphatic hydrocarbon group, the C5-C10 aryl group and the C6-C20 aralkyl group may have one or more substituents and one or more heteroatoms. Examples of the substituent include a halogen atom such as a fluorine atom and a chlorine atom, a C1-C20 alkyl group, a hydroxyl group, a nitro group, an oxo group, a cyano group, a C1-C4 acyl group such as an acetyl group and a propionyl group, a C1-C4 perfluoroalkyl group such as a trifluoromethyl group, a pentafluoroethyl group, a heptafluoropropyl group and a nonafluorobutyl group, and a C2-C5 alkoxycarbonyl group such as a methoxycarbonyl group and an ethoxycarbonyl group. Examples of the heteroatom include an oxygen atom, a sulfur atom and a nitrogen atom.

Examples of the C1-C20 aliphatic hydrocarbon group include a C1-C20 alkyl group and a C3-C20 alicyclic hydrocarbon group.

Examples of the C1-C20 alkyl group include a methyl group, an ethyl group, a propyl group, an isopropyl group, a butyl group, an isobutyl group, a sec-butyl group, a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a 2,4-dimethylhexyl group, a 2,3,6-trimethylheptyl group, a 4-ethyl-3-propyloctyl group and a 2-methoxybutyl group.
Examples of the unsubstituted or substituted C3-C20 alicyclic hydrocarbon group include the following groups represented by the formulae (R$^1$-1) to (R$^1$-77):
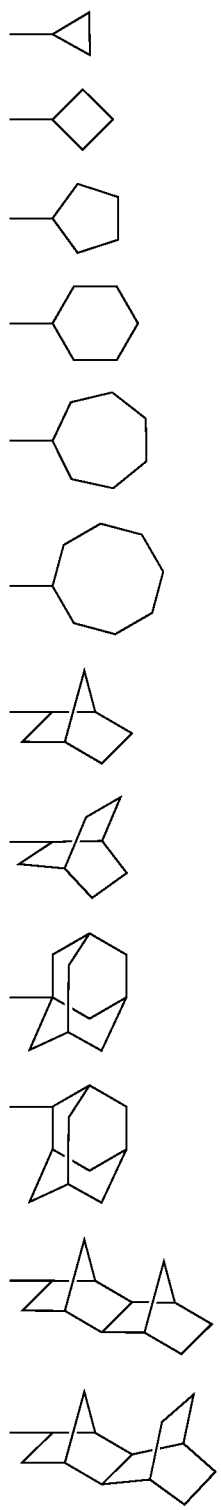
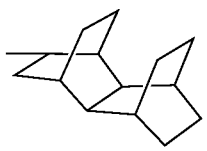
(R$^1$-13)
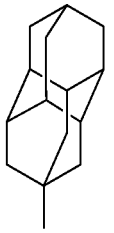
(R$^1$-14)
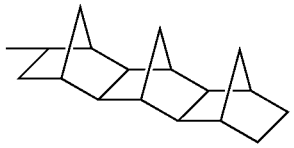
(R$^1$-15)
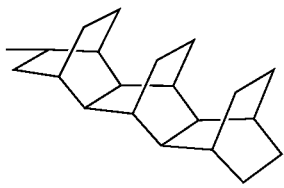
(R$^1$-16)
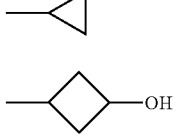
(R$^1$-17)
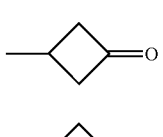
(R$^1$-18)
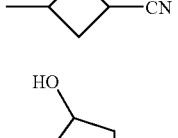
(R$^1$-19)
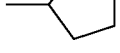
(R$^1$-20)
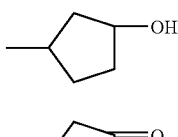
(R$^1$-21)
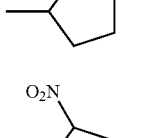
(R$^1$-22)
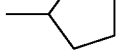
(R$^1$-23)
(R$^1$-24)

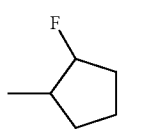 (R¹-25)
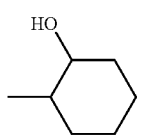 (R¹-26)
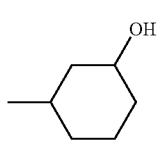 (R¹-27)
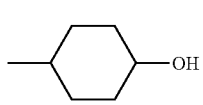 (R¹-28)
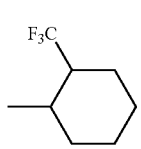 (R¹-29)
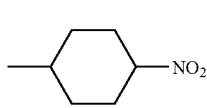 (R¹-30)
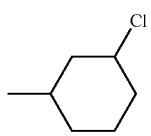 (R¹-31)
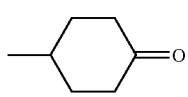 (R¹-32)
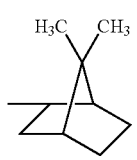 (R¹-33)
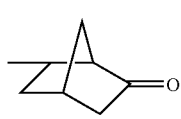 (R¹-34)
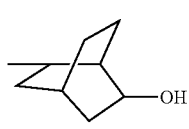 (R¹-35)
 (R¹-36)
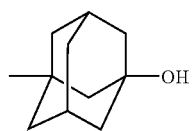 (R¹-37)
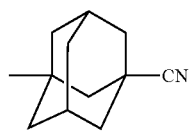 (R¹-38)
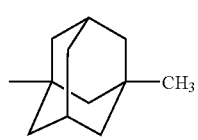 (R¹-39)
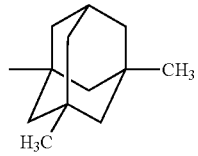 (R¹-40)
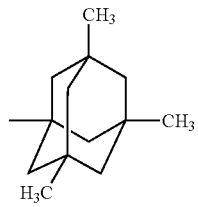 (R¹-41)
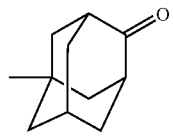 (R¹-42)
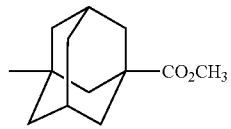 (R¹-43)
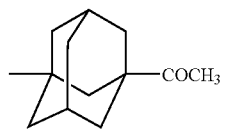 (R¹-44)
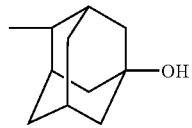 (R¹-45)
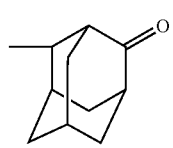 (R¹-46)

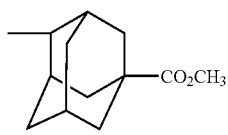 (R¹-47)
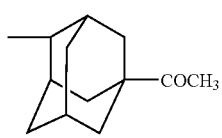 (R¹-48)
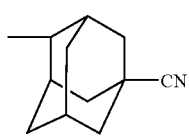 (R¹-49)
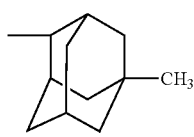 (R¹-50)
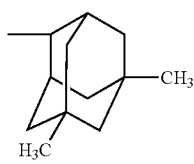 (R¹-51)
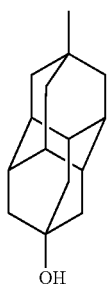 (R¹-52)
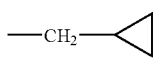 (R¹-53)
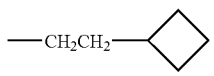 (R¹-54)
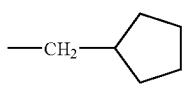 (R¹-55)
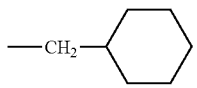 (R¹-56)
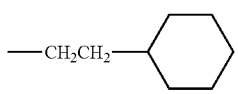 (R¹-57)
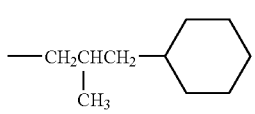 (R¹-58)
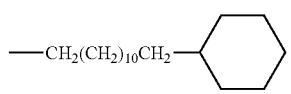 (R¹-59)
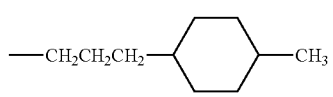 (R¹-60)
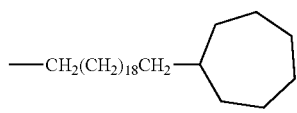 (R¹-61)
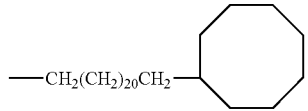 (R¹-62)
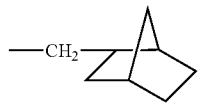 (R¹-63)
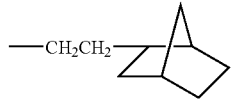 (R¹-64)
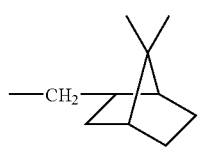 (R¹-65)
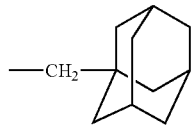 (R¹-66)
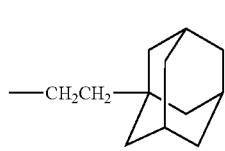 (R¹-67)
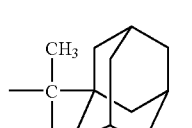 (R¹-68)
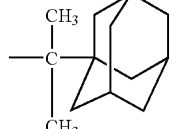 (R¹-69)
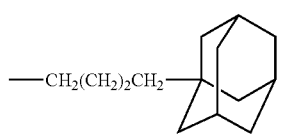 (R¹-70)

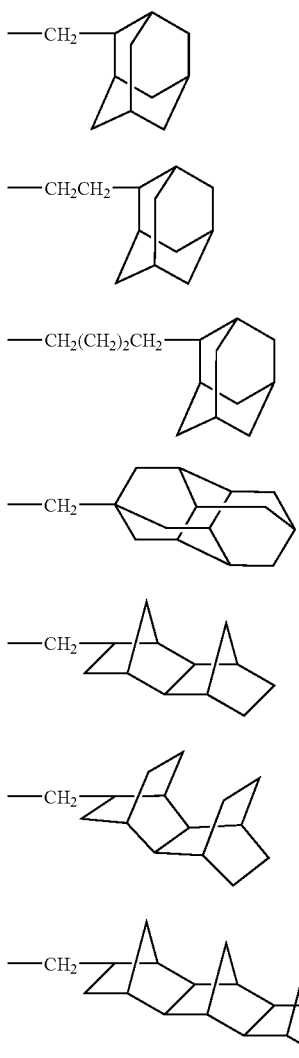
Examples of the C5-C10 aryl group which may have one or more substituents and one or more heteroatoms include the following groups represented by the formulae (R¹-78) to (R¹-94):
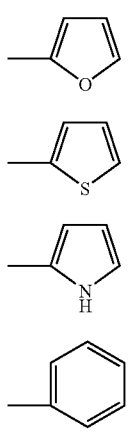
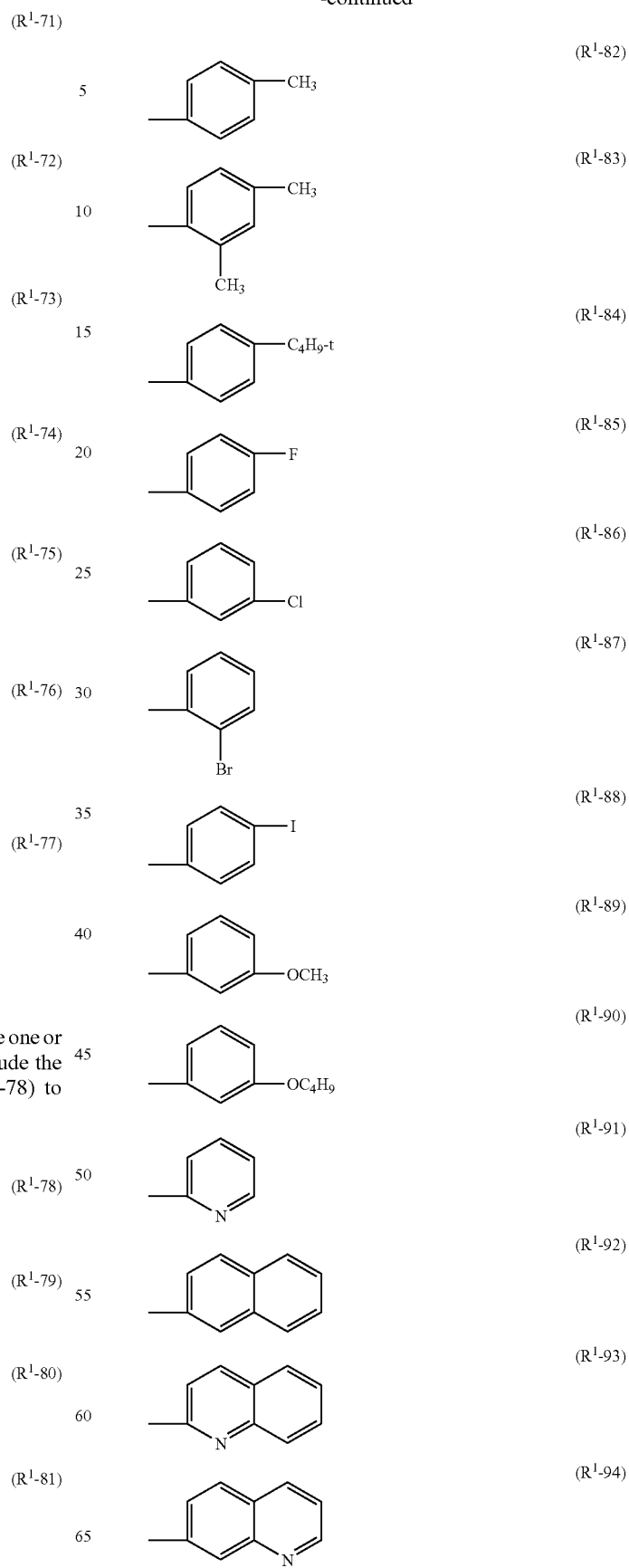

Examples of the C6-C20 aralkyl group which may have one or more substituents and one or more heteroatoms include the following groups represented by the formulae (R¹-95) to (R¹-119):

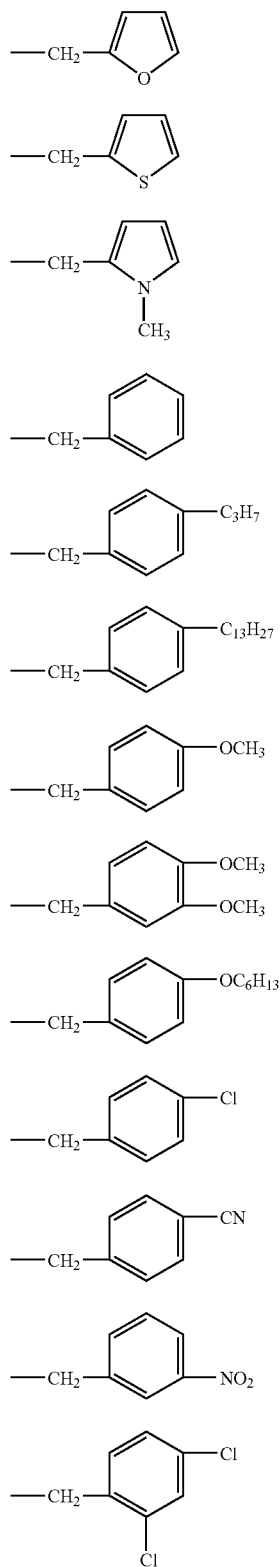
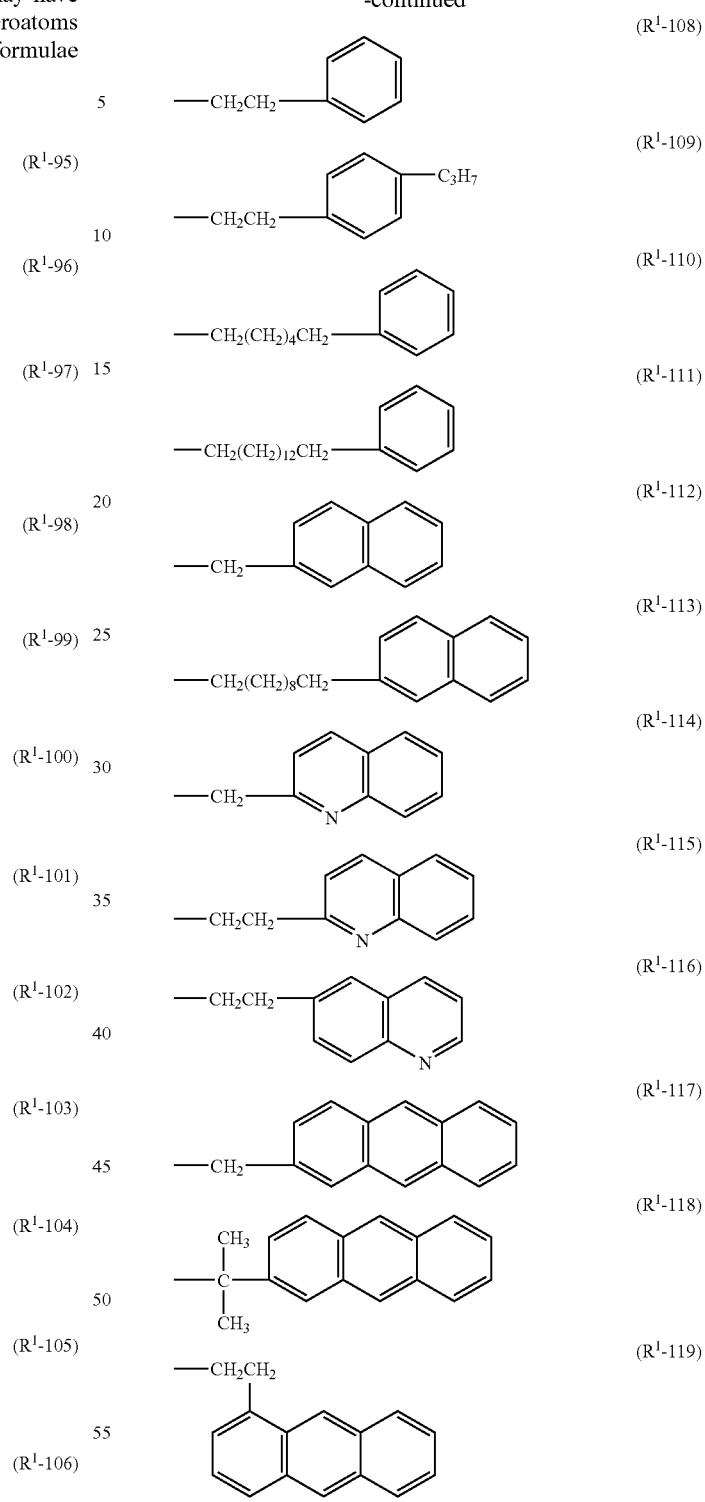

R¹ is preferably a C3-C20 alicyclic hydrocarbon group which may have one or more substituents and one or more heteroatoms.

Examples of the substituted alkyl group include a C1-C20 alkyl group substituted with an acryloyloxy group and a methacryloyloxy group wherein the C1-C20 alkyl group may have one or more substituents and one or more heteroatoms. The acryloyloxy group is preferably bonded to a terminal of the alkyl group, and a methacryloyloxy group is preferably bonded to a terminal of the alkyl group. Examples thereof include the following groups represented by the formulae ($R^1$-120) to ($R^1$-171):
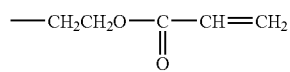 ($R^1$-120)
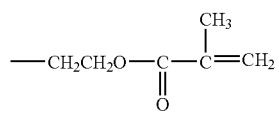 ($R^1$-121)
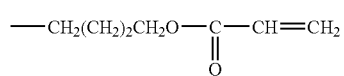 ($R^1$-122)
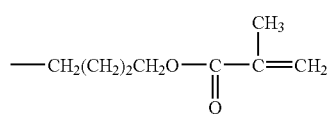 ($R^1$-123)
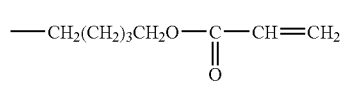 ($R^1$-124)
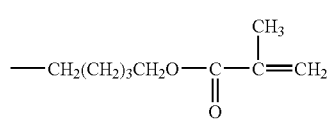 ($R^1$-125)
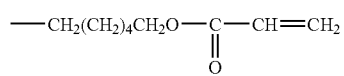 ($R^1$-126)
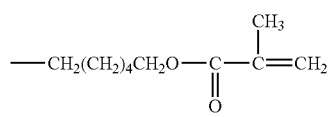 ($R^1$-127)
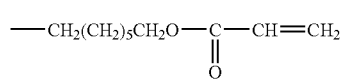 ($R^1$-128)
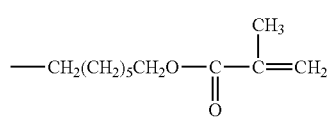 ($R^1$-129)
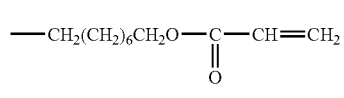 ($R^1$-130)
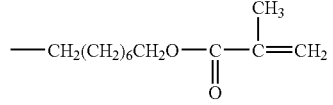 ($R^1$-131)
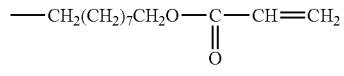 ($R^1$-132)
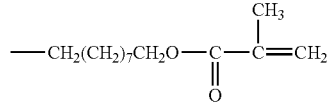 ($R^1$-133)
-continued
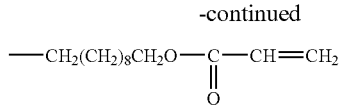 ($R^1$-134)
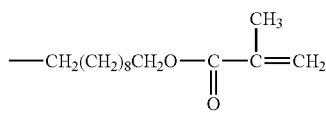 ($R^1$-135)
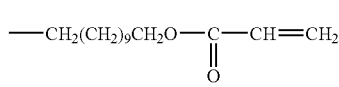 ($R^1$-136)
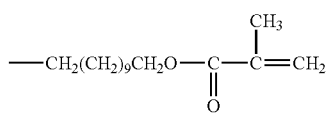 ($R^1$-137)
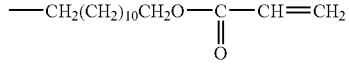 ($R^1$-138)
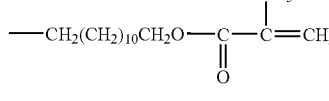 ($R^1$-139)
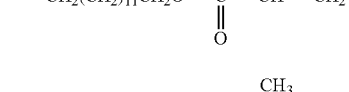 ($R^1$-140)
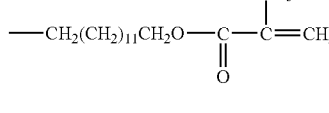 ($R^1$-141)
 ($R^1$-142)
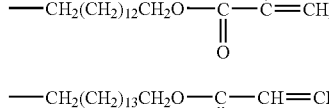 ($R^1$-143)
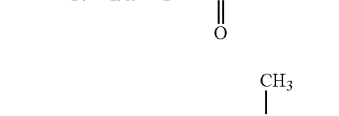 ($R^1$-144)
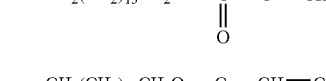 ($R^1$-145)
 ($R^1$-146)
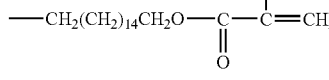 ($R^1$-147)
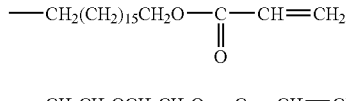 ($R^1$-148)
 ($R^1$-149)

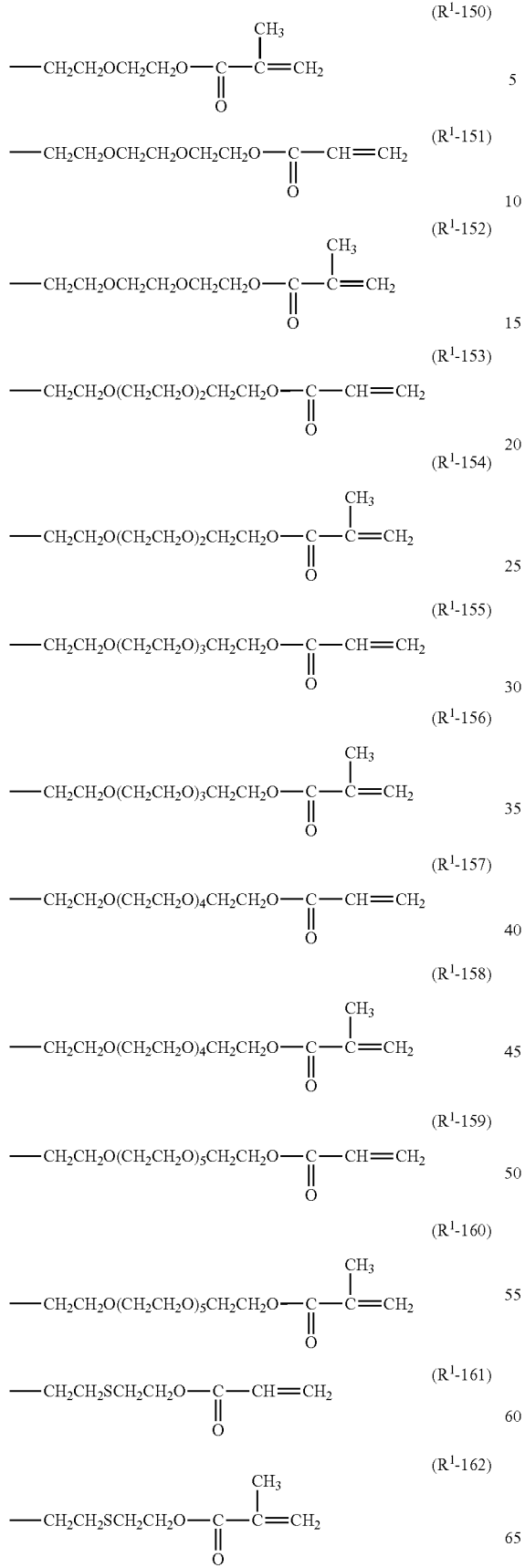
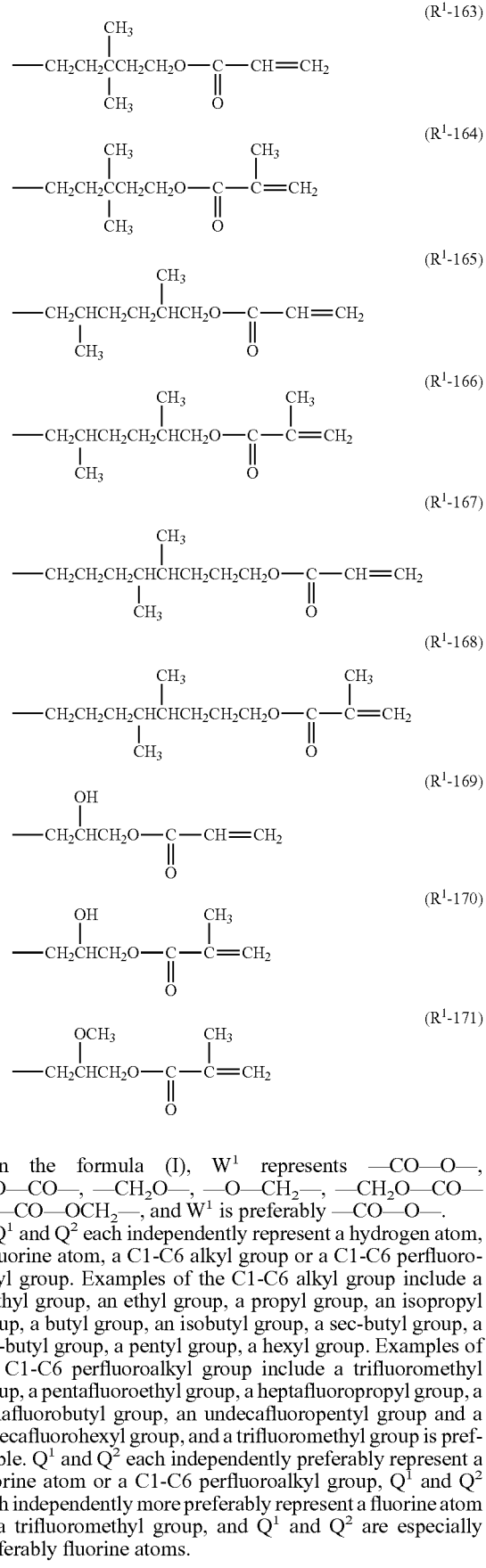

In the formula (I), $W^1$ represents —CO—O—, —O—CO—, —CH$_2$O—, —O—CH$_2$—, —CH$_2$O—CO— or —CO—OCH$_2$—, and $W^1$ is preferably —CO—O—.

$Q^1$ and $Q^2$ each independently represent a hydrogen atom, a fluorine atom, a C1-C6 alkyl group or a C1-C6 perfluoroalkyl group. Examples of the C1-C6 alkyl group include a methyl group, an ethyl group, a propyl group, an isopropyl group, a butyl group, an isobutyl group, a sec-butyl group, a tert-butyl group, a pentyl group, a hexyl group. Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Q^1$ and $Q^2$ each independently preferably represent a fluorine atom or a C1-C6 perfluoroalkyl group, $Q^1$ and $Q^2$ each independently more preferably represent a fluorine atom or a trifluoromethyl group, and $Q^1$ and $Q^2$ are especially preferably fluorine atoms.

In the formula (I), A represents a group represented by the formula (I-1):

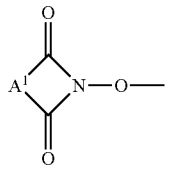
(I-1)

wherein A¹ represents —CH$_2$—CH$_2$—, —CH$_2$—CH$_2$—CH$_2$—, —CH═CH— or —CH═CH—CH$_2$—, in which one or more hydrogen atoms may be substituted with a C1-C6 aliphatic hydrocarbon group, a C3-C12 alicyclic hydrocarbon group or a C6-C10 aromatic hydrocarbon group, and the neighboring substituents may be bonded each other to form a ring, and the C1-C6 aliphatic hydrocarbon group, the C3-C12 alicyclic hydrocarbon group and the C6-C10 aromatic hydrocarbon group may have one or more substituents and one or more heteroatoms.

Examples of the substituent include a halogen atom such as a fluorine atom and a chlorine atom, a C1-C20 alkyl group, a hydroxyl group, a nitro group, an oxo group, a cyano group, a C1-C4 acyl group such as an acetyl group and a propionyl group, a C1-C4 perfluoroalkyl group such as a trifluoromethyl group, a pentafluoroethyl group, a heptafluoropropyl group and a nonafluorobutyl group, and a C2-C5 alkoxycarbonyl group such as a methoxycarbonyl group and an ethoxycarbonyl group. Examples of the heteroatom include an oxygen atom, a sulfur atom and a nitrogen atom.

Examples of the C1-C6 aliphatic hydrocarbon group include a C1-C6 alkyl group, and examples of the C1-C6 alkyl group include a methyl group, an ethyl group, a propyl group, an isopropyl group, a butyl group, an isobutyl group, a sec-butyl group, a tert-butyl group, a pentyl group and a hexyl group.

Examples of the C3-C12 alicyclic hydrocarbon group include the following groups:

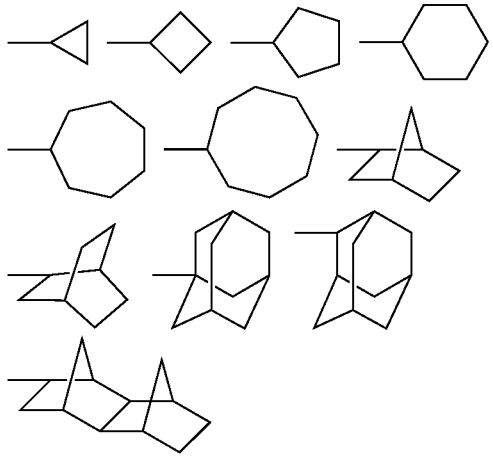

Examples of the C6-C10 aromatic hydrocarbon group include a phenyl group, a 1-naphthyl group and a 2-naphthyl group.

Examples of the group represented by the formula (I-1) wherein A¹ is —CH$_2$—CH$_2$—CH$_2$— in which one or more hydrogen atoms may be substituted with an unsubstituted or substituted C1-C6 aliphatic hydrocarbon group, an unsubstituted or substituted C3-C12 alicyclic hydrocarbon group or an unsubstituted or substituted C6-C10 aromatic hydrocarbon group include the following groups represented by the formulae (A-1) to (A-16):

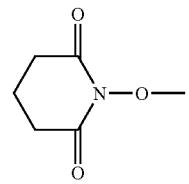
(A-1)

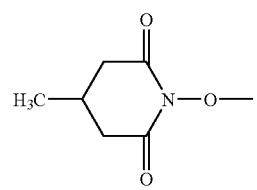
(A-2)

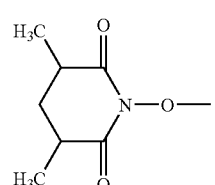
(A-3)

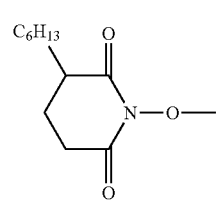
(A-4)

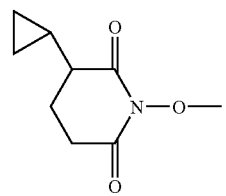
(A-5)

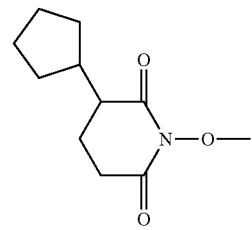
(A-6)

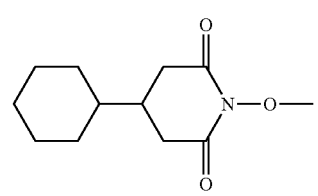
(A-7)

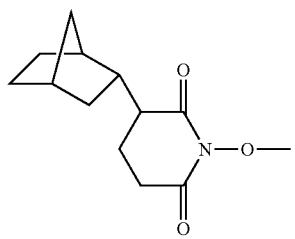
(A-8)

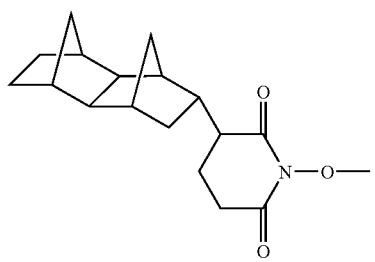
(A-9)

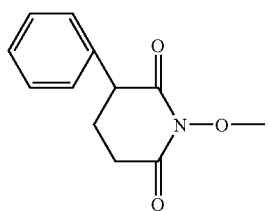
(A-10)

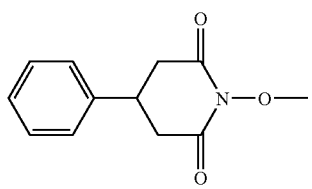
(A-11)

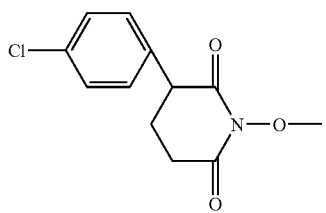
(A-12)

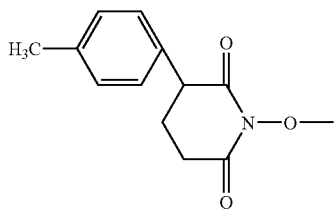
(A-13)

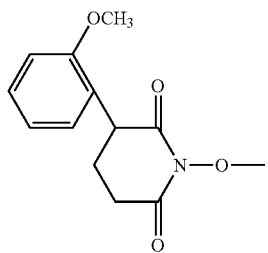
(A-14)

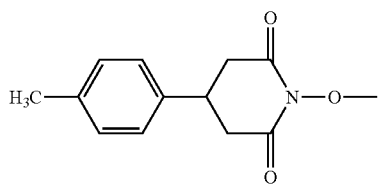
(A-15)

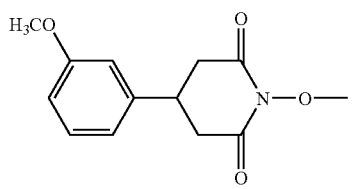
(A-16)

Examples of the group represented by the formula (I-1) wherein $A^1$ is —CH$_2$—CH$_2$—CH$_2$— in which one or more hydrogen atoms are substituted with an unsubstituted or substituted C1-C6 aliphatic hydrocarbon group, an unsubstituted or substituted C3-C12 alicyclic hydrocarbon group or an unsubstituted or substituted C6-C10 aromatic hydrocarbon group, and the neighboring substituents are bonded each other to form a ring include the following groups represented by the formulae (A-17) to (A-22):

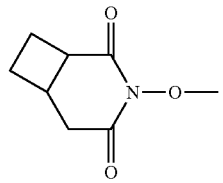
(A-17)

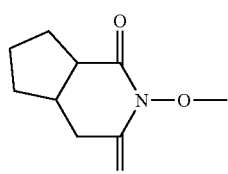
(A-18)

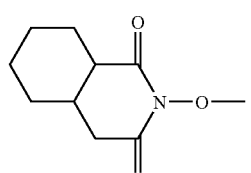
(A-19)

(A-20)

Examples of the group represented by the formula (I-1) wherein $A^1$ is —$CH_2$—$CH_2$—$CH_2$— or —CH=CH—$CH_2$— in which one or more hydrogen atoms may be substituted with an unsubstituted or substituted C1-C6 aliphatic hydrocarbon group, an unsubstituted or substituted C3-C12 alicyclic hydrocarbon group or an unsubstituted or substituted C6-C10 aromatic hydrocarbon group, and the neighboring substituents are bonded each other to form a ring include the following groups represented by the formulae (A-23) to (A-45):

(A-34)

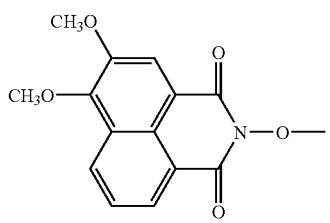

(A-35)

(A-36)

(A-37)

(A-38)

(A-39)

(A-40)

(A-41)

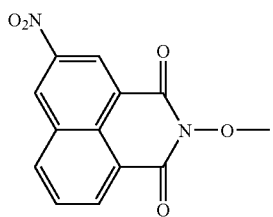

(A-42)

(A-43)

(A-44)

(A-45)

Examples of the group represented by the formula (I-1) wherein $A^1$ is —$CH_2$—$CH_2$— in which one or more hydrogen atoms may be substituted with an unsubstituted or substituted C1-C6 aliphatic hydrocarbon group, an unsubstituted or substituted C3-C12 alicyclic hydrocarbon group or an unsubstituted or substituted C6-C10 aromatic hydrocarbon group include the following groups represented by the formulae (A-46) to (A-61):

(A-46)

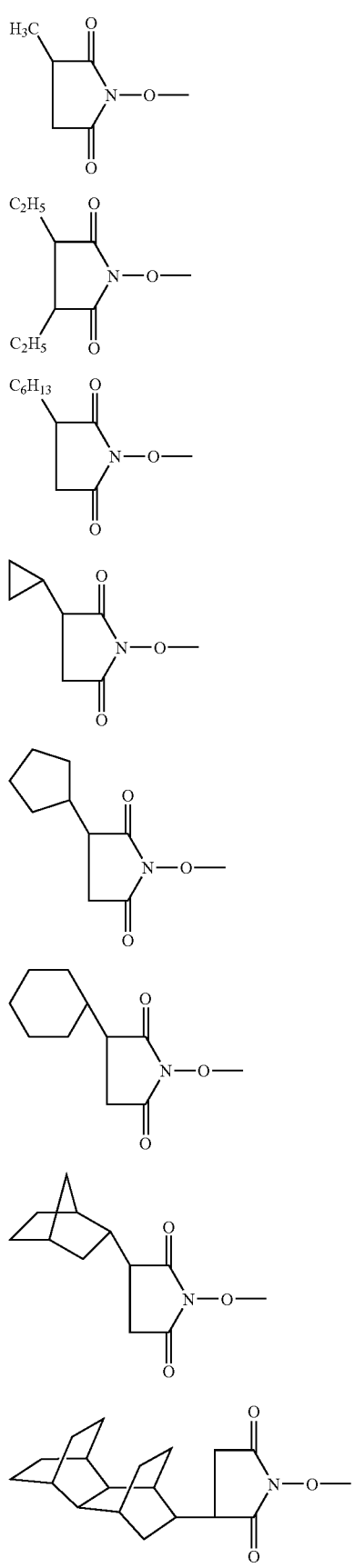
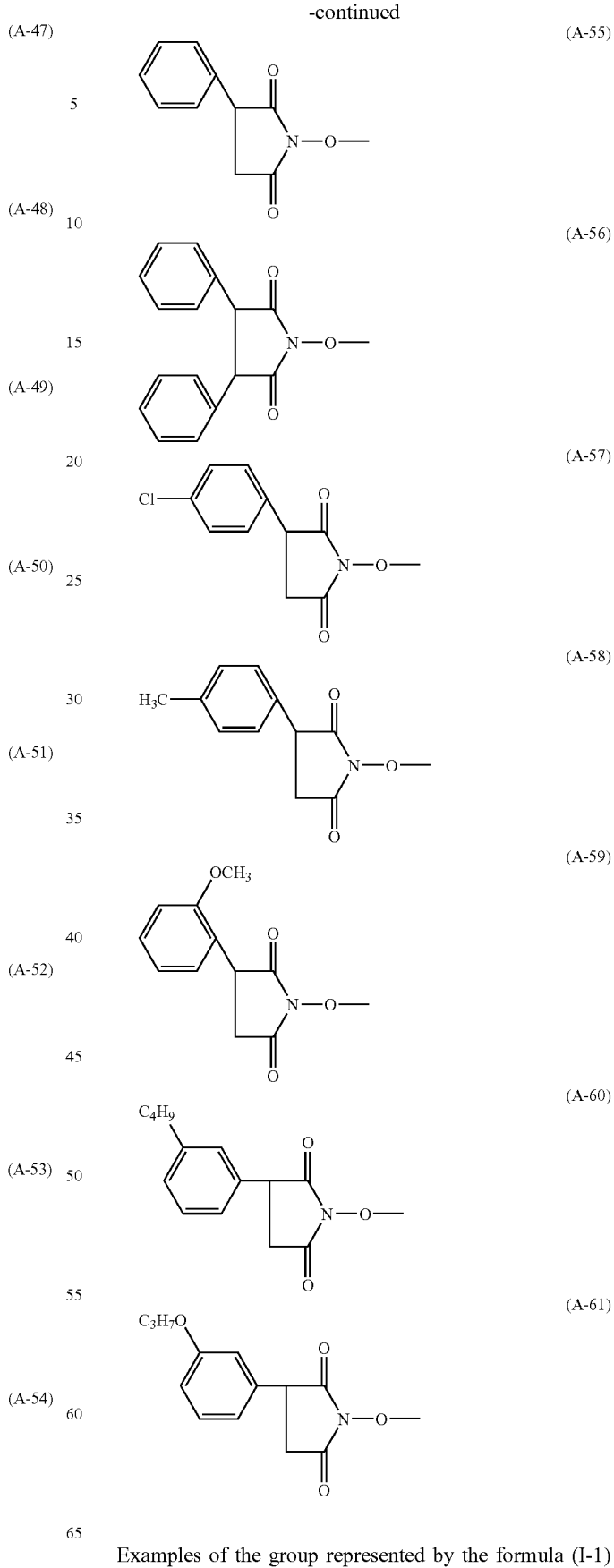
Examples of the group represented by the formula (I-1) wherein $A^1$ is —$CH_2$—$CH_2$— or —CH=CH— in which one or more hydrogen atoms may be substituted with an unsubstituted or substituted C1-C6 aliphatic hydrocarbon group, an unsubstituted or substituted C3-C12 alicyclic hydrocarbon group or an unsubstituted or substituted C6-C10 aromatic hydrocarbon group, and the neighboring substituents are bonded each other to form a ring include the following groups represented by the formulae (A-62) to (A-84):

(A-62)
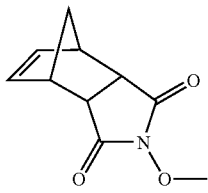

(A-63)
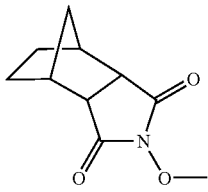

(A-64)
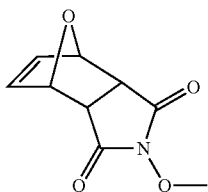

(A-65)
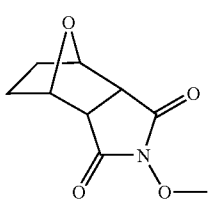

(A-66)
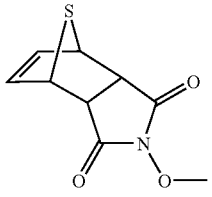

(A-67)
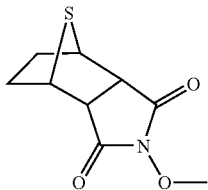

(A-68)
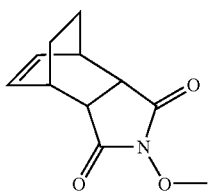

(A-69)
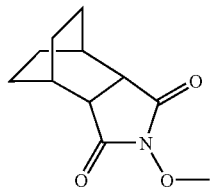

(A-70)
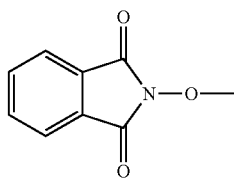

(A-71)
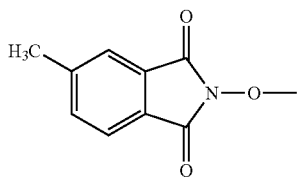

(A-72)
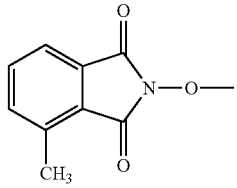

(A-73)
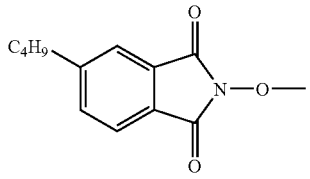

(A-74)
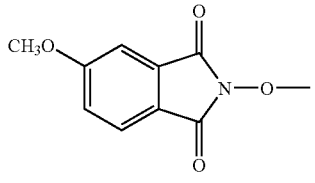

(A-75)
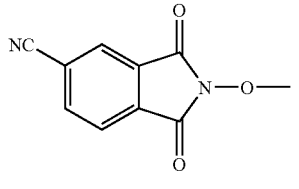

(A-76)
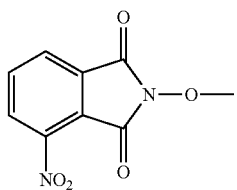

-continued

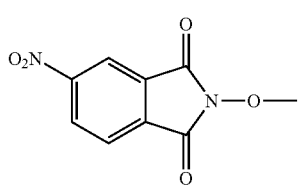
(A-77)

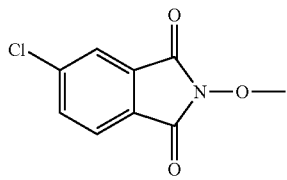
(A-78)

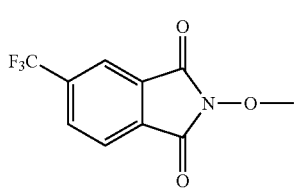
(A-79)

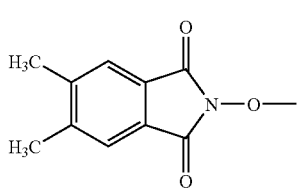
(A-80)

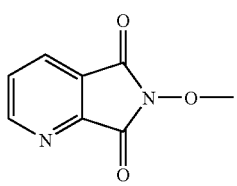
(A-81)

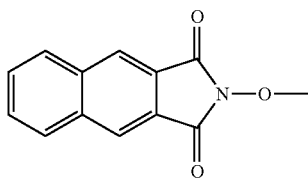
(A-82)

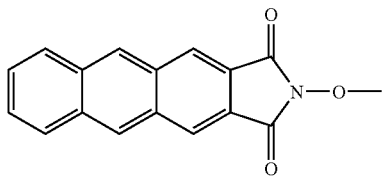
(A-83)

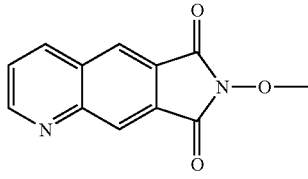
(A-84)

Examples of imide (I) include an imide compound represented by the formula (I) wherein $R^1$ is any one of the groups represented by the formulae ($R^1$-1) to ($R^1$-171), $Q^1$ and $Q^2$ are fluorine atoms, W is —CO—O—, and A is any one of the groups represented by the formulae (A-1) to (A-84).

As imide (I), a compound represented by the formula (III), (IV), (V), (VI) or (VII):

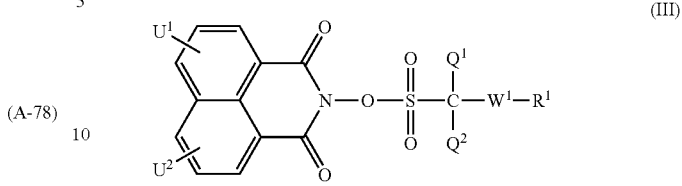
(III)

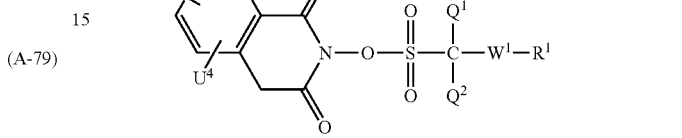
(IV)

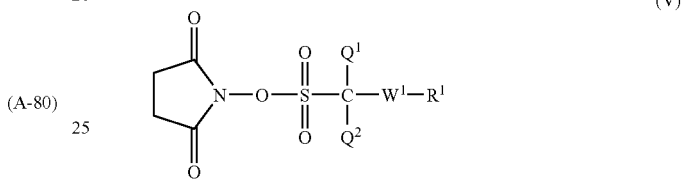
(V)

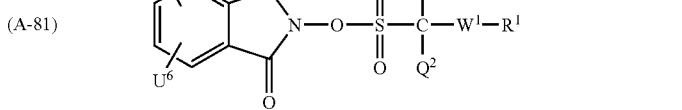
(VII)

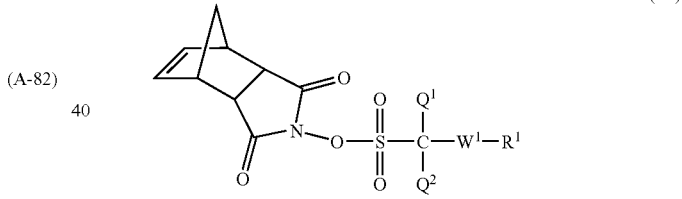
(VI)

wherein $U^1$ to $U^6$ each independently represent a hydrogen atom, a C1-C4 hydrocarbon group or a C1-C4 alkoxy group, and $R^1$, $W^1$, $Q^1$ and $Q^2$ are the same meanings as defined above, is preferable.

Specific examples of imide (I) include the followings:

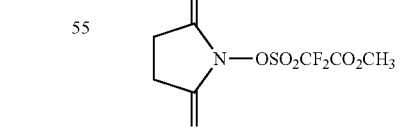

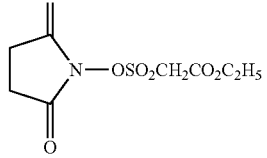

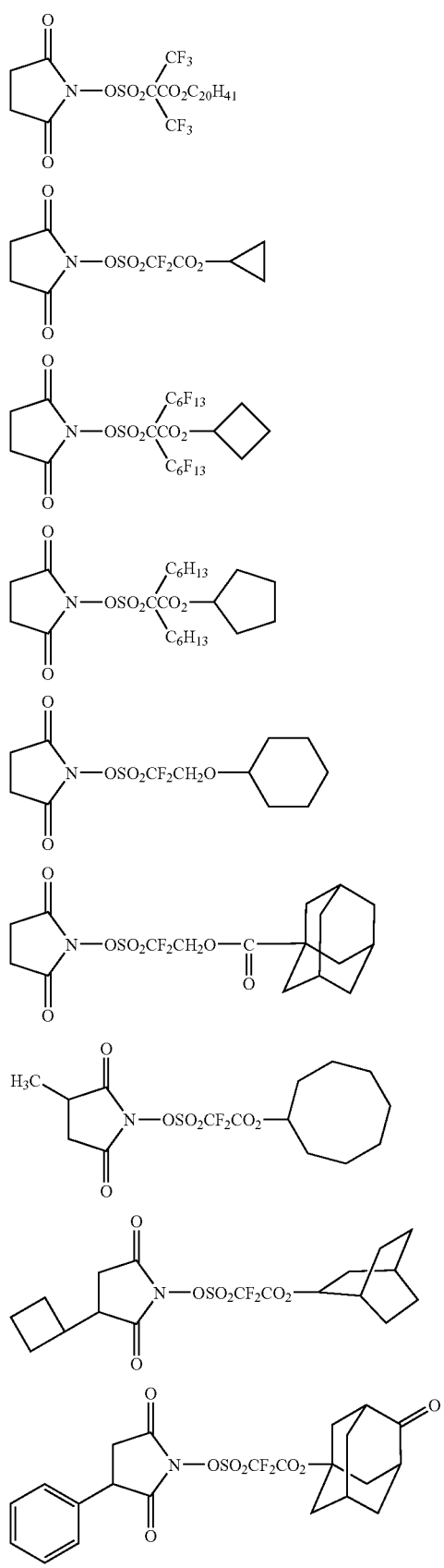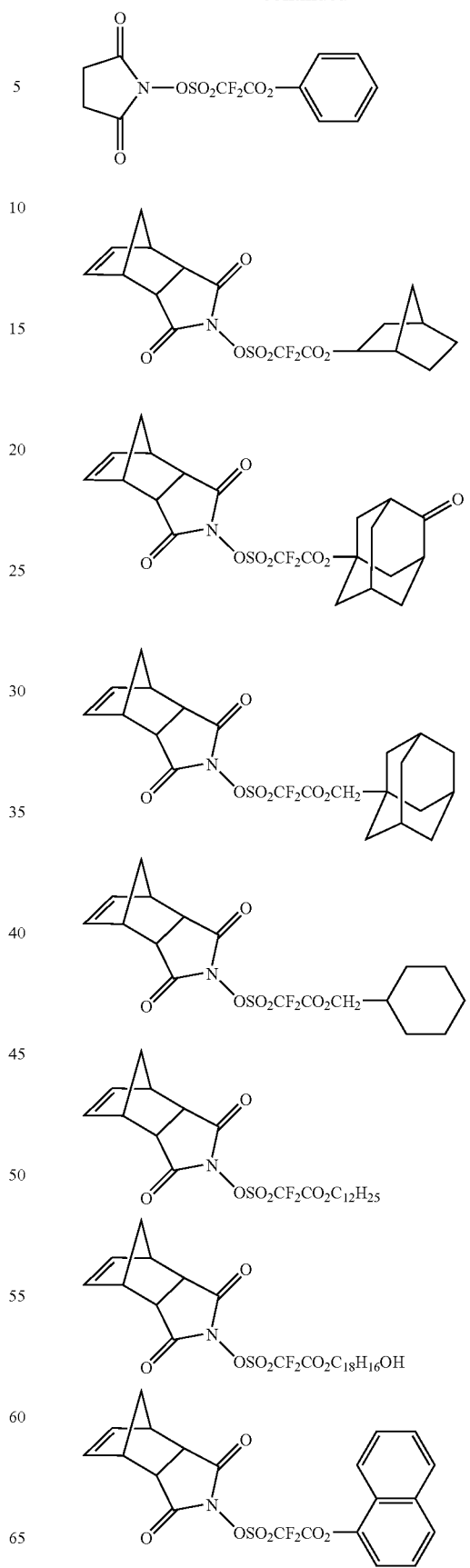

35
-continued
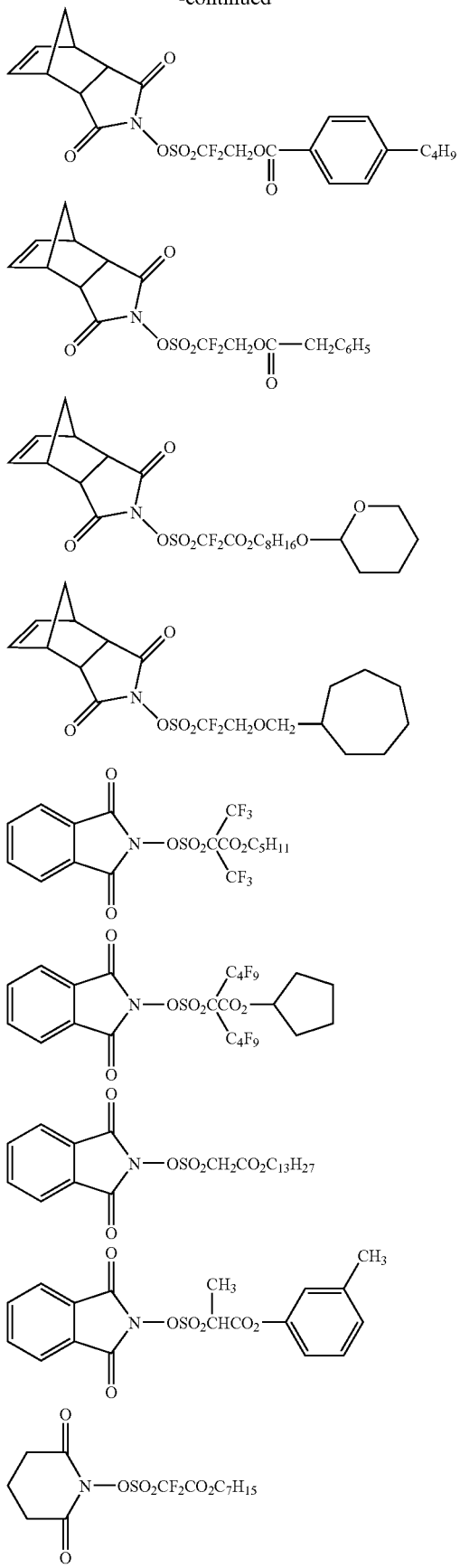
36
-continued
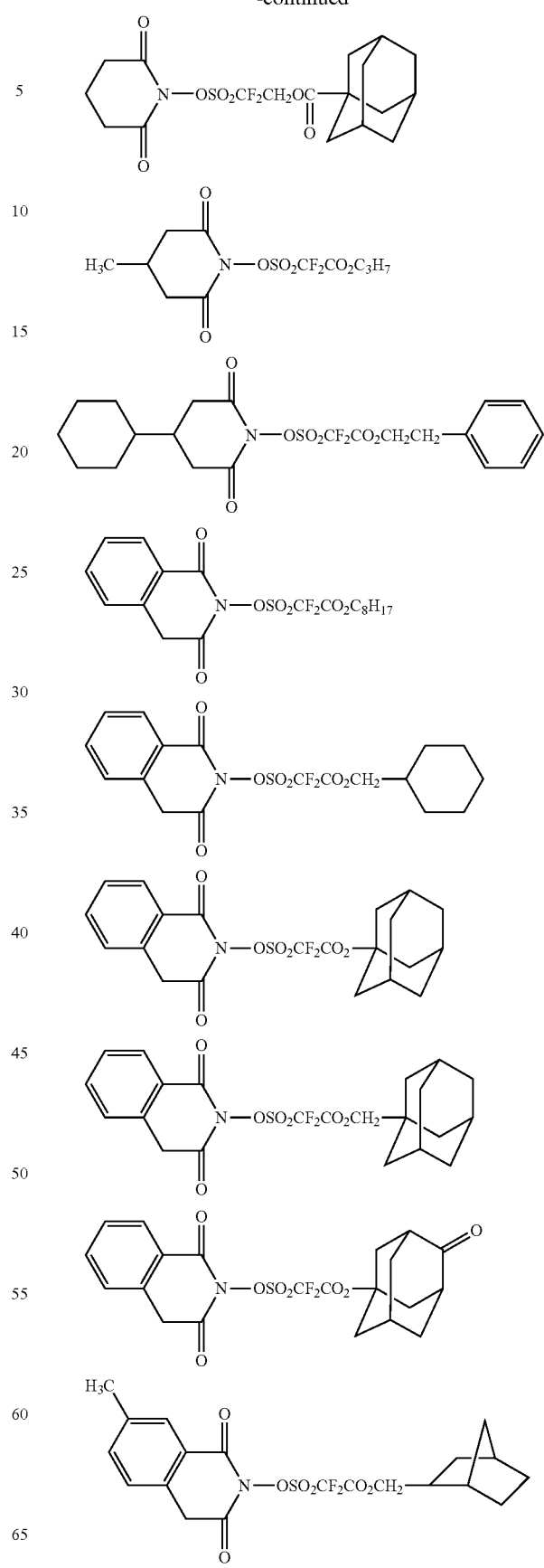

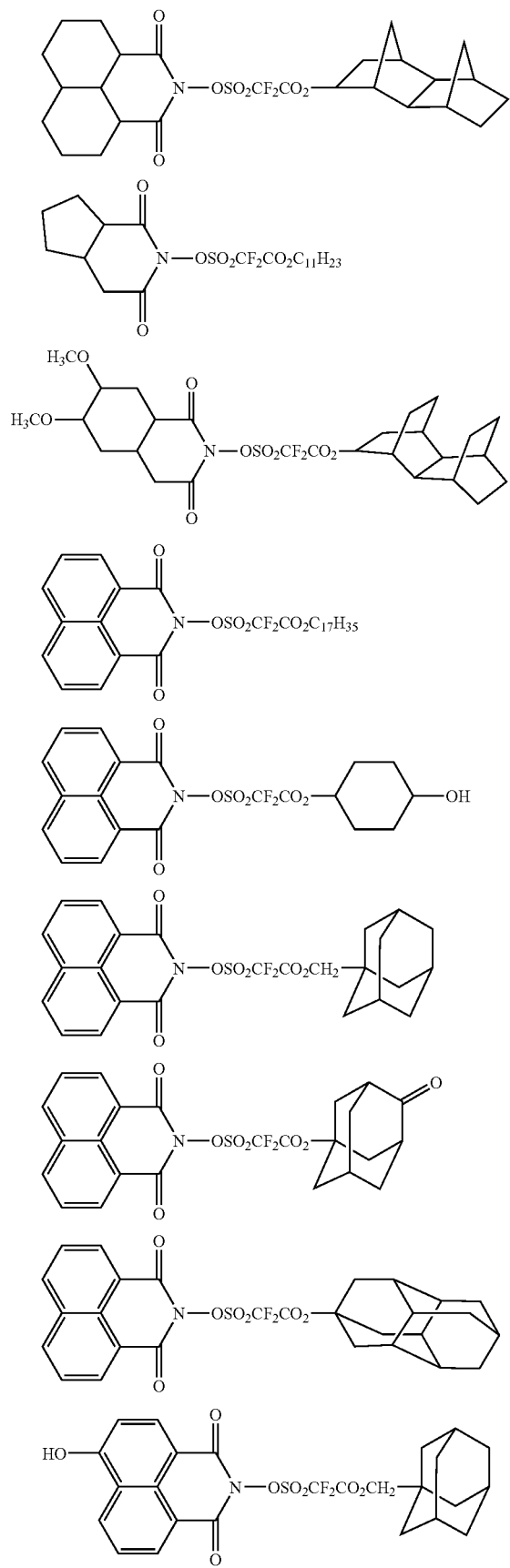
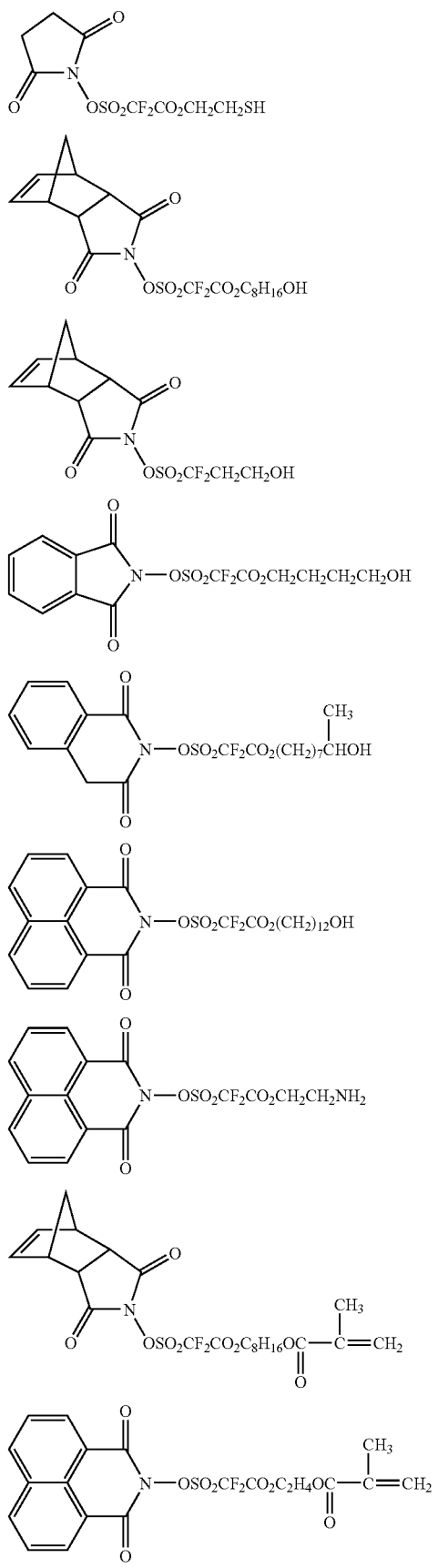

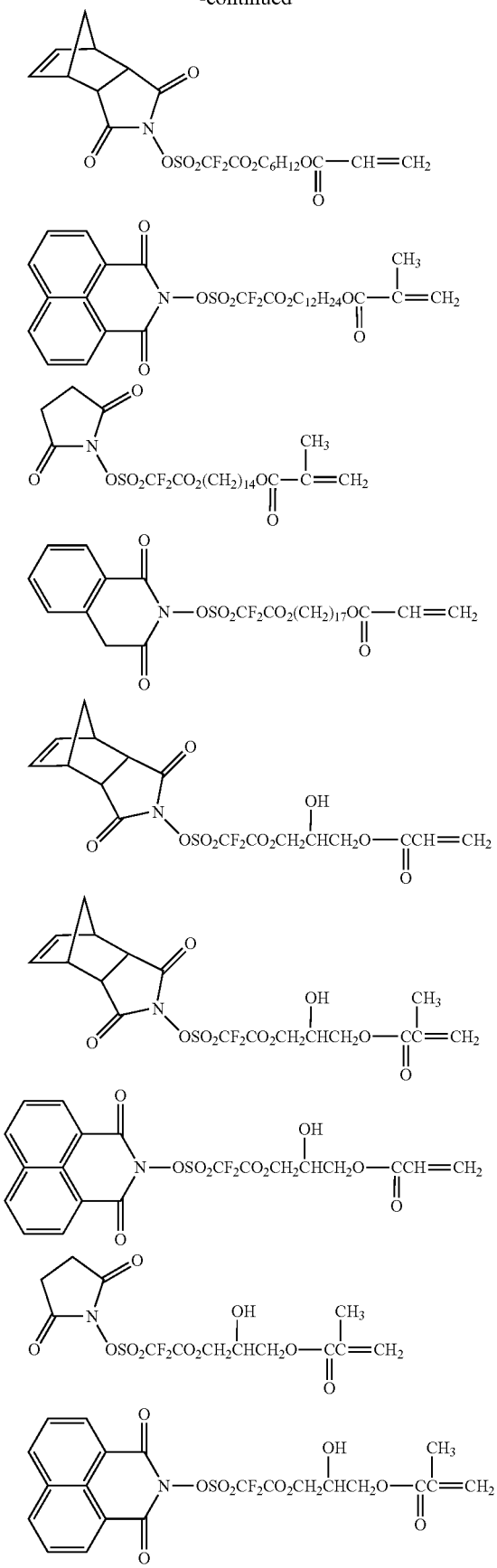
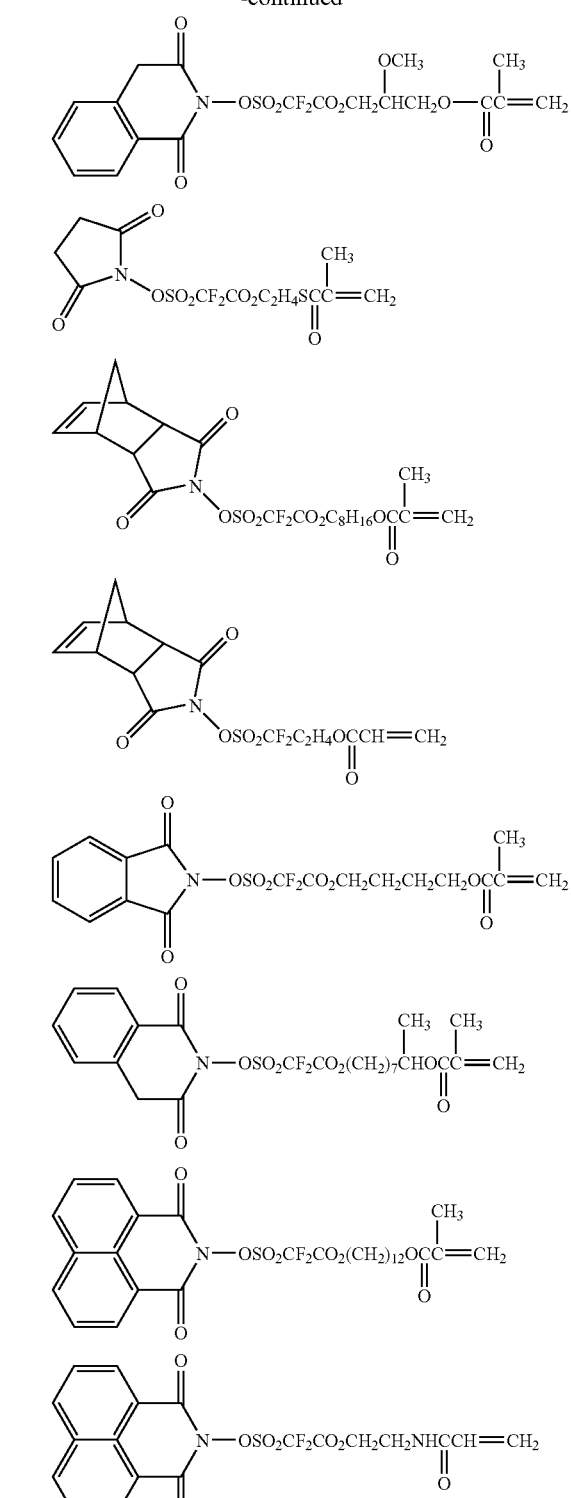
Imide (I) can be produced by reacting a compound represented by the formula (VIII):
$$A-H \quad \quad (VIII)$$
wherein A is the same as defined above, with a compound represented by the formula (IX):

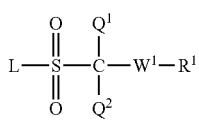

(IX)

wherein $R^1$, $W^1$, $Q^1$ and $Q^2$ are the same meanings as defined above, and L represents a halogen atom, in the presence of a base.

The reaction is preferably conducted in an inert solvent such as toluene, tetrahydrofuran, N,N-dimethylformamide, dimethylsulfoxide, acetonitrile, chloroform and dichloromethane.

The reaction temperature is usually about 0 to 150° C. and preferably about 0 to 100° C., and the reaction is preferably conducted with stirring.

Examples of the halogen atom represented by L include a fluorine atom, a chlorine atom, a bromine atom and an iodine atom.

The amount of the compound represented by the formula (IX) is usually about 0.9 to 2 moles and preferably 1 to 1.5 moles per 1 mole of the compound represented by the formula (VIII).

Examples of the base include an inorganic base such as sodium hydroxide, potassium hydroxide and potassium carbonate, and an organic base such as pyridine, triethylamine and lutidine. The amount of the base is usually 1 to 3 moles and preferably 1 to 2 moles per 1 mole of the compound represented by the formula (VIII).

Imide (I) obtained by the process above can be isolated by conducting extraction followed by concentrating, and isolated imide (I) can be purified by recrystallization or column chromatography.

The resist composition of the present invention comprises a resin and imide (I).

Examples of the resin include a resin comprising a structural unit having an acid-labile group and being insoluble or poorly soluble in an aqueous alkali solution but becoming soluble in an aqueous alkali solution by the action of an acid.

Imide (I) works as an acid generator.

In this specification, "an acid-labile group" means a group capable to eliminate by the action of an acid.

In this specification, "—COOR" may be described as "a structure having ester of carboxylic acid", and may also be abbreviated as "ester group". Specifically, "—COOC(CH$_3$)$_3$" may be described as "a structure having tert-butyl ester of carboxylic acid", or be abbreviated as "tert-butyl ester group".

Examples of the acid-labile group include a structure having ester of carboxylic acid such as alkyl ester group in which a carbon atom adjacent to the oxygen atom is quaternary carbon atom, alicyclic ester group in which a carbon atom adjacent to the oxygen atom is quaternary carbon atom, and a lactone ester group in which a carbon atom adjacent to the oxygen atom is quaternary carbon atom. The "quaternary carbon atom" means a "carbon atom joined to four substituents other than hydrogen atom". Other examples of the acid-labile group include a group having a quaternary carbon atom joined to three carbon atoms and an —OR', wherein R' represents an alkyl group.

Examples of the acid-labile group include an alkyl ester group in which a carbon atom adjacent to the oxygen atom is quaternary carbon atom such as a tert-butyl ester group; an acetal type ester group such as a methoxymethyl ester, ethoxymethyl ester, 1-ethoxyethyl ester, 1-isobutoxyethyl ester, 1-isopropoxyethyl ester, 1-ethoxypropoxy ester, 1-(2-methoxyethoxy)ethyl ester, 1-(2-acetoxyethoxy)ethyl ester, 1-[2-(1-adamantyloxy)ethoxy]ethyl ester, 1-[2-(1-adamantanecarbonyloxy)ethoxy]ethyl ester, tetrahydro-2-furyl ester and tetrahydro-2-pyranyl ester group; an alicyclic ester group in which a carbon atom adjacent to the oxygen atom is quaternary carbon atom, such as an isobornyl ester, 1-alkylcycloalkyl ester, 2-alkyl-2-adamantyl ester and 1-(1-adamantyl)-1-alkylalkyl ester group. At least one hydrogen atom in the adamantyl group may be substituted with a hydroxyl group.

Examples of the structural unit having an acid-labile group include a structure unit derived from an ester of acrylic acid, a structural unit derived from an ester of methacrylic acid, a structural unit derived from an ester of norbornenecarboxylic acid, a structural unit derived from an ester of tricyclodecenecarboxylic acid and a structural unit derived from an ester of tetracyclodecenecarboxylic acid. The structure units derived from the ester of acrylic acid and from the ester of methacrylic acid are preferable.

The resin used for the present composition can be obtained by conducting polymerization reaction of a monomer or monomers having the acid-labile group and an olefinic double bond.

Among the monomers, those having a bulky and acid-labile group such as an alicyclic ester group (e.g. a 2-alkyl-2-adamantyl ester and 1-(1-adamantyl)-1-alkylalkyl ester group) are preferable, since excellent resolution is obtained when the resin obtained is used in the present resist composition.

Examples of such monomer containing the bulky and acid-labile group include a 2-alkyl-2-adamantyl acrylate, a 2-alkyl-2-adamantyl methacrylate, 1-(1-adamantyl)-1-alkylalkyl acrylate, a 1-(1-adamantyl)-1-alkylalkyl methacrylate, a 2-alkyl-2-adamantyl 5-norbornene-2-carboxylate, a 1-(1-adamantyl)-1-alkylalkyl 5-norbornene-2-carboxylate, a 2-alkyl-2-adamantyl α-chloroacrylate and a 1-(1-adamantyl)-1-alkylalkyl α-chloroacrylate.

Particularly when the 2-alkyl-2-adamantyl acrylate, the 2-alkyl-2-adamantyl methacrylate or the 2-alkyl-2-adamantyl α-chloroacrylate is used as the monomer for the resin component in the present resist composition, a resist composition having excellent resolution tend to be obtained. Typical examples thereof include 2-methyl-2-adamantyl acrylate, 2-methyl-2-adamantyl methacrylate, 2-ethyl-2-adamantyl acrylate, 2-ethyl-2-adamantyl methacrylate, 2-n-butyl-2-adamantyl acrylate, 2-methyl-2-adamantyl α-chloroacrylate and 2-ethyl-2-adamantyl α-chloroacrylate.

When particularly 2-ethyl-2-adamantyl acrylate, 2-ethyl-2-adamantyl methacrylate, 2-isopropyl-2-adamantyl acrylate or 2-isopropyl-2-adamantyl methacrylate is used for the present resist composition, a resist composition having excellent sensitivity and heat resistance tends to be obtained. In the present invention, two or more kinds of monomers having a group or groups dissociated by the action of the acid may be used together, if necessary.

The 2-alkyl-2-adamantyl acrylate can be usually produced by reacting a 2-alkyl-2-adamantanol or a metal salt thereof with an acrylic halide, and the 2-alkyl-2-adamantyl methacrylate can be usually produced by reacting a 2-alkyl-2-adamantanol or a metal salt thereof with a methacrylic halide.

The resin used for the present resist composition can also contain other structural unit or units derived from an acid-stable monomer in addition to the above-mentioned structural units having the acid-labile group. Herein, the "structural unit derived from an acid-stable monomer" means "a structural unit not dissociated by an acid.

Examples of such other structural unit derived from the acid-stable monomer include a structural unit derived from a monomer having a free carboxyl group such as acrylic acid and methacrylic acid; a structural unit derived from an aliphatic unsaturated dicarboxylic anhydride such as maleic anhydride and itaconic anhydride; a structural unit derived from 2-norbornene; a structural unit derived from acrylonitrile or methacrylonitrile; a structural unit derived from an alkyl acrylate or an alkyl methacrylate in which a carbon atom adjacent to oxygen atom is secondary or tertiary carbon atom; a structural unit derived from 1-adamantyl acrylate or 1-adamantyl methacrylate; a structural unit derived from styrene monomer such as p-hydroxystyrene and m-hydroxystyrene; a structural unit derived from acryloyloxy-γ-butyrolactone or methacryloyloxy-γ-butyrolactone having a lactone ring which may be substituted with an alkyl group; and the like. Herein, the 1-adamantyloxycarbonyl group is the acid-stable group though the carbon atom adjacent to oxygen atom is the quaternary carbon atom, and the 1-adamantyloxycarbonyl group may be substituted with at least one hydroxyl group.

Specific examples of the structural unit derived from the acid-stable monomer include a structural unit derived from 3-hydroxy-1-adamantyl acrylate;

a structural unit derived from 3-hydroxy-1-adamantyl methacrylate;

a structural unit derived from 3,5-dihydroxy-1-adamantyl acrylate;

a structural unit derived from 3,5-dihydroxy-1-adamantyl methacrylate;

a structural unit derived from α-acryloyloxy-γ-butyrolactone;

a structural unit derived from α-methacryloyloxy-γ-butyrolactone;

a structural unit derived from β-acryloyloxy-γ-butyrolactone;

a structural unit derived from β-methacryloyloxy-γ-butyrolactone;

a structural unit represented by the formula (k1):

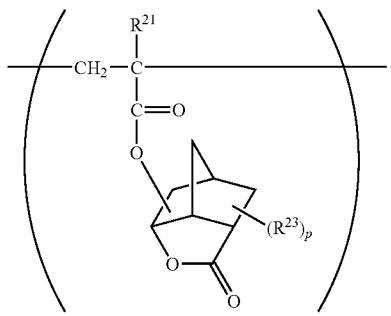

(k1)

wherein $R^{21}$ represents a hydrogen atom or a methyl group, $R^{23}$ is independently in each occurrence a methyl group, a trifluoromethyl group or a halogen atom, and p represents an integer of 0 to 3;

a structural unit represented by the formula (k2):

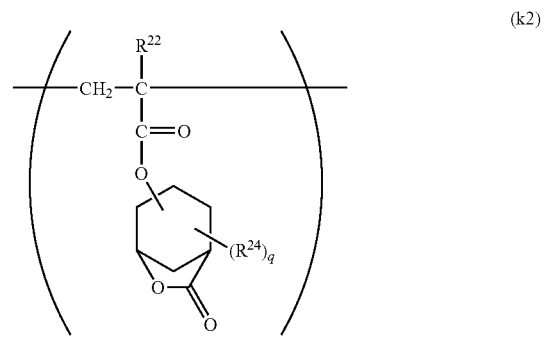

(k2)

wherein $R^2$ represents a hydrogen atom or a methyl group, $R^{24}$ is independently in each occurrence a methyl group, a trifluoromethyl group or a halogen atom, and q represents an integer of 0 to 3;

a structural unit derived from p-hydroxystyrene;

a structural unit derived from m-hydroxystyrene;

a structural unit derived from an alicyclic compound having an olefinic double bond such as a structural unit represented by the formula (k3):

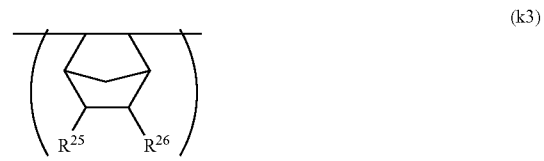

(k3)

wherein $R^{25}$ and $R^{26}$ each independently represents a hydrogen atom, a C1-C3 alkyl group, a C1-C3 hydroxyalkyl group, a carboxyl group, a cyano group, a hydroxyl group or a —COOU group in which U represents an alcohol residue, or $R^{25}$ and $R^{26}$ can be bonded together to form a carboxylic anhydride residue represented by —C(=O)OC(=O)—;

a structural unit derived from an aliphatic unsaturated dicarboxylic anhydride such as a structural unit represented by the formula (k4):

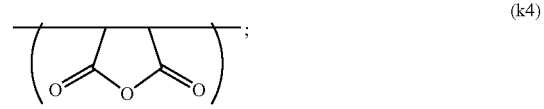

(k4)

a structural unit represented by the formula (5):

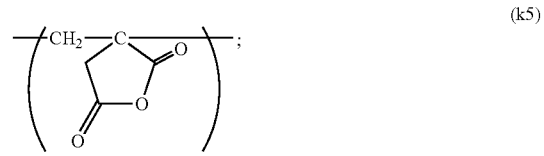

(k5)

a structural unit derived from a bridged diester of acrylic acid or methacrylic acid such as ethylene diester of acrylic acid, ethylene diester of methacrylic acid, oxydiethylene diester of acrylic acid and oxydiethylene diester of methacrylic acid.

Particularly, the resin having further at least one structural unit selected from the group consisting of the structural unit derived from p-hydroxystyrene, the structural unit derived from m-hydroxystyrene, the structural unit derived from 3-hydroxy-1-adamantyl acrylate, the structural unit derived from 3-hydroxy-1-adamantyl methacrylate, the structural unit derived from 3,5-dihydroxy-1-adamantyl acrylate, the structural unit derived from 3,5-dihydroxy-1-adamantyl methacrylate, the structural unit represented by the formula (k1) and the structural unit represented by the formula (k2) in addition to the structural unit having the acid-labile group is preferable from the standpoint of the adhesiveness of resist to a substrate and resolution of resist.

3-Hydroxy-1-adamantyl acrylate, 3-hydroxy-1-adamantyl methacrylate, 3,5-dihydroxy-1-adamantyl acrylate and 3,5-dihydroxy-1-adamantyl methacrylate can be produced, for example, by reacting corresponding hydroxyadamantane with acrylic acid, methacrylic acid or its acid halide, and they are also commercially available.

Further, the acryloyloxy-γ-butyrolactone and the methacryloyloxy-γ-butyrolactone can be produced by reacting corresponding α- or β-bromo-γ-butyrolactone with acrylic acid or methacrylic acid, or reacting corresponding α- or β-hydroxy-γ-butyrolactone with the acrylic halide or the methacrylic halide.

Examples of the monomers to give structural units represented by the formulae (k1) and (k2) include an acrylate of alicyclic lactones and a methacrylate of alicyclic lactones having the hydroxyl group described below, and mixtures thereof. These esters can be produced, for example, by reacting the corresponding alicyclic lactone having the hydroxyl group with acrylic acid or methacrylic acid, and the production method thereof is described in, for example, JP 2000-26446 A.

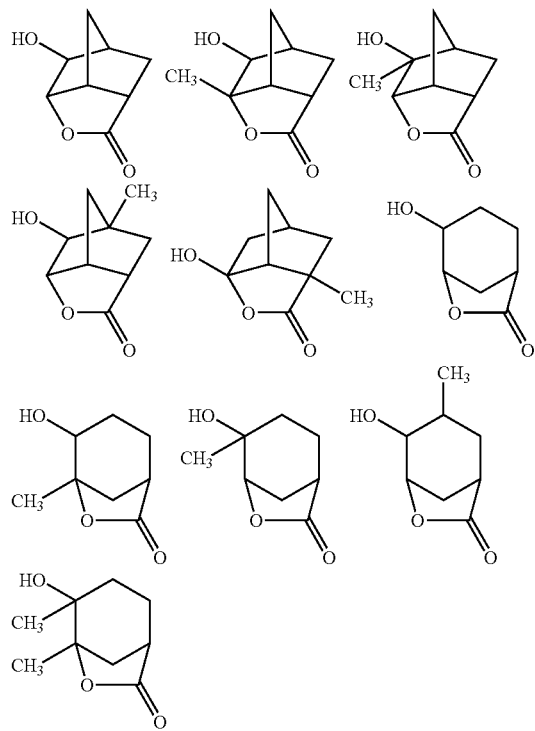

Examples of the acryloyloxy-γ-butyrolactone and the methacryloyloxy-γ-butyrolactone in which lactone ring may be substituted with the alkyl group include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone, and β-methacryloyloxy-α-methyl-γ-butyrolactone.

In the case of KrF lithography, even in the case of using a structure unit derived from hydroxystyrene such as p-hydroxystyrene and m-hydroxystyrene, as one of components of the resin, a resist composition having sufficient transparency can be obtained. For obtaining such copolymerization resins, the corresponding acrylic or methacrylic ester monomer can be radical-polymerized with acetoxystyrene and styrene, and then the acetoxy group in the structure unit derived from acetoxystyrene can be de-acetylated with an acid.

The resin containing a structural unit derived from 2-norbornene shows strong structure because the alicyclic group is directly present on its main chain and shows a property that dry etching resistance is excellent. The structural unit derived from 2-norbornene can be introduced into the main chain by radical polymerization using, for example, an aliphatic unsaturated dicarboxylic anhydride such as maleic anhydride and itaconic anhydride together in addition to corresponding 2-norbornene. The structural unit derived from 2-norbornene is formed by opening of its double bond, and can be represented by the above-mentioned formula (k3). The structural units derived from maleic anhydride and from itaconic anhydride which are the structural unit derived from aliphatic unsaturated dicarboxylic anhydrides are formed by opening of their double bonds, and can be represented by the above-mentioned formula (k4) and the formula (k5), respectively.

In $R^{25}$ and $R^{26}$, examples of the C1-C3 alkyl group include a methyl, ethyl, and n-propyl group, and examples of the C1-C3 hydroxyalkyl group include a hydroxymethyl and 2-hydroxyethyl group.

In $R^{25}$ and $R^{26}$, the —COOU group is an ester formed from the carboxyl group, and examples of the alcohol residue corresponding to U include an optionally substituted C1-C8 alkyl group, 2-oxooxolan-3-yl group and 2-oxooxolan-4-yl group, and examples of the substituent on the C1-C8 alkyl group include a hydroxyl group and an alicyclic hydrocarbon.

Specific examples of the monomer used to give the structural unit represented by the above-mentioned formula (k3) may include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When U in the —COOU group is the acid-labile group, the structural unit represented by the formula (k3) is a structural unit having the acid-labile group even if it has the norbornane structure. Examples of monomers giving a structural unit having the acid-labile group include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate and 1-(1-adamantyl)-1-methylethyl 5-norbornene-2-carboxylate.

The resin used in the present composition preferably contains the structural unit having an acid-labile group generally in a ratio of 10 to 80% by mole in all structural units of the resin though the ratio varies depending on the kind of radiation for patterning exposure, the kind of the acid-labile group, and the like.

When the structural units particularly derived from the 2-alkyl-2-adamantyl acrylate, the 2-alkyl-2-adamantyl methacrylate, the 1-(1-adamantyl)-1-alkylalkyl acrylate or the 1-(1-adamantyl)-1-alkylalkyl methacrylate are used as the structural unit having the acid-labile group, it is advantageous in dry-etching resistance of the resist that the ratio of said structural units is 15% by mole or more in all structural units of the resin.

The resin may have a structural unit derived from imide (I) wherein $R^1$ is a C1-C20 alkyl group substituted with an acryloyloxy group or a methacryloyloxy group and the C1-C20 alkyl group may have one or more substituents and one or more heteroatoms.

The resin used in the present invention can be usually produced by conducting a polymerization reaction of the corresponding monomer or monomers. The resin can be also produced by conducting an oligomerization reaction of the corresponding monomer or monomers followed by polymerizing the oligomer obtained.

The polymerization reaction is usually carried out in the presence of a radical initiator.

The radical initiator is not limited and examples thereof include an azo compound such as 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile), 2,2'-azobis(2,4-dimethyl-4-methoxyvaleronitrile), dimethyl-2,2'-azobis(2-methylpropionate) and 2,2'-azobis(2-hydroxymethylpropionitrile); an organic hydroperoxide such as lauroyl peroxide, tert-butyl hydroperoxide, benzoyl peroxide, tert-butyl peroxybenzoate, cumene hydroperoxide, diisopropyl peroxydicarbonate, di-n-propyl peroxydicarbonate, tert-butyl peroxyneodecanoate, tert-butyl peroxypivalate and 3,5,5-trimethylhexanoyl peroxide; and an inorganic peroxide such as potassium peroxodisulfate, ammonium peroxodisulfate and hydrogen peroxide. Among them, the azo compound is preferable and 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile) and dimethyl-2,2'-azobis(2-methylpropionate) are more preferable.

These radical initiators may be used alone or in a form of a mixture of two or more kinds thereof. When the mixture of two or more kinds thereof is used, the mixed ratio is not limited.

The amount of the radical initiator is preferably 1 to 20% by mole based on all monomer or oligomer molar amount.

The polymerization temperature is usually 0 to 150° C., and preferably 40 to 100° C.

The polymerization reaction is usually carried out in the presence of a solvent and it is preferred to use a solvent which is sufficient to dissolve the monomer, the radical initiator and the resin obtained. Examples thereof include a hydrocarbon solvent such as toluene; an ether solvent such as 1,4-dioxane and tetrahydrofuran; a ketone solvent such as methyl isobutyl ketone; an alcohol solvent such as isopropyl alcohol; a cyclic ester solvent such as γ-butyrolactone; a glycol ether ester ester solvent such as propylene glycol monomethyl ether acetate; and an acyclic ester solvent such as ethyl lactate. These solvents may be used alone and a mixture thereof may be used.

The amount of the solvent is not limited, and practically, it is preferably 1 to 5 parts by weight relative to 1 part of all monomers or oligomers.

When an alicyclic compound having an olefinic double bond and an aliphatic unsaturated dicarboxylic anhydride are used as monomers, it is preferable to use them in excess amount in view of a tendency that these are not easily polymerized.

After completion of the polymerization reaction, the resin produced can be isolated, for example, by adding a solvent in which the present resin is insoluble or poorly soluble to the reaction mixture obtained and filtering the precipitated resin. If necessary, the isolated resin may be purified, for example, by washing with a suitable solvent.

The polymer of the present invention comprises a structural unit derived from imide (I) wherein $R^1$ is a C1-C20 alkyl group substituted with an acryloyloxy group or a methacryloyloxy group and the C1-C20 alkyl group may have one or more substituents and one or more heteroatoms, and it is a novel polymer.

The present polymer may consist of the structural unit derived from imide (I) wherein $R^1$ is a C1-C20 alkyl group substituted with an acryloyloxy group or a methacryloyloxy group and the C1-C20 alkyl group may have one or more substituents and one or more heteroatoms, and may contain other structural unit or units in addition to the structural unit derived from imide (I) wherein $R^1$ is a C1-C20 alkyl group substituted with an acryloyloxy group or a methacryloyloxy group and the C1-C20 alkyl group may have one or more substituents and one or more heteroatoms.

Examples of the other structural unit include a structural unit having an acid-labile group, a structural unit having an acid-stable group. Examples of the structural unit having an acid-labile group and the structural unit having an acid-stable group include the same as described above.

When the polymer of the present invention contains the structural unit having an acid-labile group, the ratio of the structural unit derived from imide (I) wherein $R^1$ is a C1-C20 alkyl group substituted with an acryloyloxy group or a methacryloyloxy group and the C1-C20 alkyl group may have one or more substituents and one or more heteroatoms, is usually 0.1 to 70% by mole and preferably 1 to 50% by mole in all structural units of the present polymer.

The polymer of the present invention can be prepared by polymerizing imide (I) wherein $R^1$ is a C1-C20 alkyl group substituted with an acryloyloxy group or a methacryloyloxy group and the C1-C20 alkyl group may have one or more substituents and one or more heteroatoms, or polymerizing imide (I) wherein $R^1$ is a C1-C20 alkyl group substituted with an acryloyloxy group or a methacryloyloxy group and the C1-C20 alkyl group may have one or more substituents and one or more heteroatoms and the other monomer or monomers.

This polymerization reaction can be conducted according to the polymerization reaction described above.

The resist composition of the present invention may contain the polymer of the present invention, and may contain the above-mentioned resin and the polymer of the present invention.

As described above, imide (I) works as an acid generator. Alternatively, the present polymer also works as an acid generator.

The resist composition of the present invention also contains the other acid generators).

The acid generator is a substance which is decomposed to generate an acid by applying a radiation such as a light, an electron beam or the like on the substance itself or on a resist composition containing the substance. The acid generated from the acid generator acts on the resin and/or the present polymer resulting in cleavage of the acid-labile group existing in the resin and/or the present polymer.

Examples of the acid generator include an onium salt compound, an organo-halogen compound, a sulfone compound and a sulfonate compound. The onium salt compound is preferable.

The acid generators described in JP 2003-5374 A1 can be also used in the present resist composition.

Examples of the onium salt compound include diphenyliodonium trifluoromethanesulfonate, 4-methoxyphenylphenyliodonium hexafluoroantimonate, 4-methoxyphenylphenyliodonium trifluoromethanesulfonate, bis(4-tert-butylphenyl)iodonium tetrafluoroborate, bis(4-tert-butylphenyl)iodonium hexafluorophosphate, bis(4-tert-butylphenyl)iodonium hexafluoroantimonate, bis(4-tert-butylphenyl)iodonium trifluoromethanesulfonate, triphenylsulfonium hexafluorophosphate, triphenylsulfonium hexafluoroantimonate, triphenylsulfonium trifluoromethanesulfonate, triphenylsulfonium adamantylmethoxycarbonyldifluoromethanesulfonate, triphenylsulfonium (3-hydroxyadamantyl)methoxycarbonyldifluoromethanesulfonate, triphenylsulfonium 1-(3-hydroxymethyladamantyl)methoxycarbonyldifluoromethanesulfonate, triphenylsulfonium 1-(hexahydro-2-oxo-3,5-methano-2H-cyclopenta[b]furan-6-yloxy carbonyl)difluoromethanesulfonate, triphenylsulfonium 4-oxo-1-adamantyloxycarbonyldifluoromethanesulfonate, 4-methoxyphenyldiphenylsulfonium hexafluoroantimonate, 4-methoxyphenyldiphenylsulfonium trifluoromethanesulfonate, p-tolyldiphenylsulfonium trifluoromethanesulfonate, p-tolyldiphenylsulfonium heptadecafluorooctanesulfonate, 2,4,6-trimethylphenyldiphenylsulfonium trifluoromethanesulfonate, 4-tert-butylphenyldiphenylsulfonium trifluoromethanesulfonate, 4-phenylthiophenyldiphenylsulfonium hexafluorophosphate, 4-phenylthiophenyldiphenylsulfonium hexafluoroantimonate, 1-(2-naphthoylmethyl)thiolanium hexafluoroantimonate, 1-(2-naphthoylmethyl)thiolanium trifluoromethanesulfonate, 4-hydroxy-1-naphthyldimethylsulfonium hexafluoroantimonate and 4-hydroxy-1-naphthyldimethylsulfonium trifluoromethanesulfonate.

Examples of the organic halide compound include 2-methyl-4,6-bis(trichloromethyl)-1,3,5-triazine, 2,4,6-tris(trichloromethyl)-1,3,5-triazine, 2-phenyl-4,6-bis(trichloromethyl)-1,3,5-triazine, 2-(4-chlorophenyl)-4,6-bis(trichloromethyl)-1,3,5-triazine, 2-(4-methoxyphenyl)-4,6-bis(trichloromethyl)-1,3,5-triazine, 2-(4-methoxy-1-naphthyl)-4,6-bis(trichloromethyl)-1,3,5-triazine, 2-(benzo[d][1,3]dioxoran-5-yl)-4,6-bis(trichloromethyl)-1,3,5-triazine, 2-(4-methoxystyryl)-4,6-bis(trichloromethyl)-1,3,5-triazine, 2-(3,4,5-trimethoxystyryl)-4,6-bis(trichloromethyl)-1,3,5-triazine, 2-(3,4-dimethoxystyryl)-4,6-bis(trichloromethyl)-1,3,5-triazine, 2-(2,4-dimethoxyxtyryl)-4,6-bis(trichloromethyl)-1,3-triazine, 2-(2-methoxystyryl)-4,6-bis(trichloromethyl)-1,3,5-triazine, 2-(4-butoxystyryl)-4,6-bis(trichloromethyl)-1,3,5-triazine and 2-(4-pentyloxystyryl)-4,6-bis(trichloromethyl)-1,3,5-triazine.

Examples of the sulfone compound include diphenyl disulfone, di-p-tolyl disulfone, bis(phenylsulfonyl)diazomethane, bis(4-chlorophenylsulfonyl)diazomethane, bis(p-tolylsulfonyl)diazomethane, bis(4-tert-butylphenylsulfonyl)diazomethane, bis(2,4-xylylsulfonyl)diazomethane, bis(cyclohexylsulfonyl)diazomethane, (benzoyl)(phenylsulfonyl)diazomethane, N-(phenylsulfonyloxy)succinimide, N-(trifluoromethylsulfonyloxy)succinimide, N-(trifluoromethylsulfonyloxy)phthalimide, N-(trifluoromethylsulfonyloxy)-5-norbornene-2,3-dicarbodiimide, N-(trifluoromethylsulfonyloxy)naphthalimide and N-(10-camphorsulfonyloxy)naphthalimide.

Examples of the sulfonate compound include 1-benzoyl-1-phenylmethyl p-toluenesulfonate, 2-benzoyl-2-hydroxy-2-phenylethyl o-toluenesulfonate, 1,2,3-benzenetriyl tris-methansulfonate, 2,6-dinitrobenzyl p-toluenesulfonate, 2-nitrobenzyl p-toluenesulfonate and 4-nitrobenzyl p-toluenesulfonate.

The present resist composition preferably includes 80 to 99.9% by weight of the resin component and 0.1 to 20% by weight of the acid generator component. Herein, "acid generator component" contains imide (I), the present polymer, the other acid generator(s) or a mixture thereof.

When the resist composition contains the present polymer comprising the structural unit derived from imide (I) wherein $R^1$ is a C1-C20 alkyl group substituted with an acryloyloxy group or a methacryloyloxy group and the C1-C20 alkyl group may have one or more substituents and one or more heteroatoms, and the other acid generators, the ratio of the present polymer and the other acid generator(s) is not limited.

In the present resist composition, performance deterioration caused by inactivation of acid which occurs due to post exposure delay can be diminished by adding an organic base compound, particularly a nitrogen-containing organic base compound as a quencher.

Specific examples of the nitrogen-containing organic base compound include an amine compound represented by the following formulae:

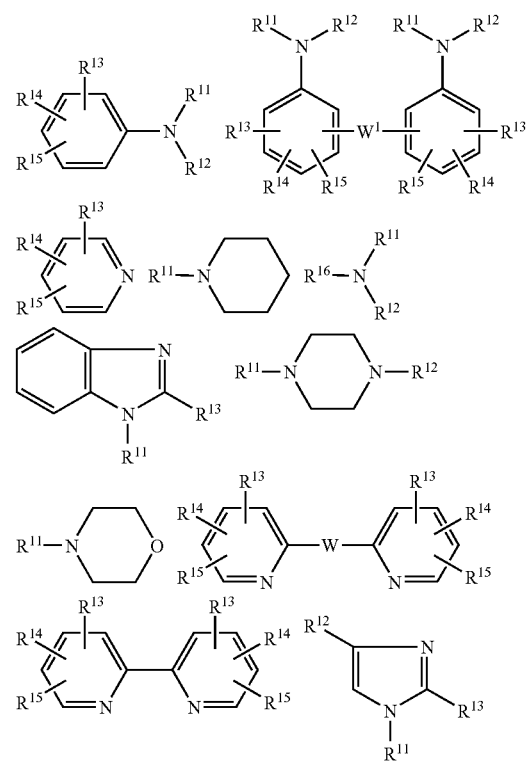

wherein $R^{11}$ and $R^{12}$ independently represent a hydrogen atom, an alkyl group, a cycloalkyl group or an aryl group, and the alkyl, cycloalkyl and aryl groups may be substituted with at least one group selected from the group consisting of a hydroxyl group, an amino group which may be substituted with a C1-C4 alkyl group and a C1-C6 alkoxy group which may be substituted with a C1-C8 alkoxy group, $R^{13}$ and $R^{14}$ independently represent a hydrogen atom, an alkyl group, a cycloalkyl group, an aryl group or an alkoxy group, and the alkyl, cycloalkyl, aryl and alkoxy groups may be substituted with at least one group selected from the group consisting of a hydroxyl group, an amino group which may be substituted with a C1-C4 alkyl group and a C1-C6 alkoxy group, or $R^{13}$ and $R^{14}$ bond together with the carbon atoms to which they bond to form an aromatic ring, $R^{15}$ represent a hydrogen atom, an alkyl group, a cycloalkyl group, an aryl group, an alkoxy group or a nitro group, and the alkyl, cycloalkyl, aryl and alkoxy groups which may be substituted with at least one group selected from the group consisting of a hydroxyl group, an amino group which may be substituted with a C1-C4 alkyl group and a C1-C6 alkoxy group, $R^{16}$ represents an alkyl or cycloalkyl group, and the alkyl and cycloalkyl groups may be substituted with at least one group selected from the group consisting of a hydroxyl group, an amino group which may be substituted with a C1-C4 alkyl group and a C1-C6 alkoxy group, and W represents —CO—, —NH—, —S—, —S—S—, an alkylene group of which at least one methylene group may be replaced with —O—, or an alkenylene group of which at least one methylene group may be replaced with —O—, and a quaternary ammonium hydroxide represented by the following formula:

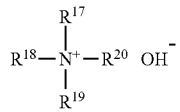

wherein $R^{17}$, $R^{18}$, $R^{19}$ and $R^{20}$ independently represent an alkyl group, a cycloalkyl group or an aryl group, and the alkyl, cycloalkyl and aryl groups may be substituted with at least one group selected from the group consisting of a hydroxyl group, an amino group which may be substituted with a C1-C4 alkyl group and a C1-C6 alkoxy group.

The alkyl group in $R^{11}$, $R^{12}$, $R^{13}$, $R^{14}$, $R^{15}$, $R^{16}$, $R^{17}$, $R^{18}$, $R^{19}$ and $R^{20}$ preferably has about 1 to 10 carbon atoms, and more preferably has about 1 to 6 carbon atoms.

Examples of the amino group which may be substituted with the C1-C4 alkyl group include an amino group, a methylamino group, an ethylamino group, an n-butylamino group, a dimethylamino group and a diethylamino group. Examples of the C1-C6 alkoxy group which may be substituted with the C1-C6 alkoxy group include a methoxy group, an ethoxy group, an n-propoxy group, an isopropoxy group, an n-butoxy group, a tert-butoxy group, an n-pentyloxy group, an n-hexyloxy group and a 2-methoxyethoxy group.

Specific examples of the alkyl group which may be substituted with at least one group selected from the group consisting of a hydroxyl group, an amino group which may be substituted with a C1-C4 alkyl group, and a C1-C6 alkoxy group which may be substituted with a C1-C6 alkoxy group include a methyl group, an ethyl group, an n-propyl group, an isopropyl group, an n-butyl group, a tert-butyl group, an n-pentyl group, an n-hexyl group, an n-octyl group, an n-nonyl group, an n-decyl group, a 2-(2-methoxyethoxy) ethyl group, a 2-hydroxyethyl group, a 2-hydroxypropyl group, a 2-aminoethyl group, a 4-aminobutyl group and a 6-aminohexyl group.

The cycloalkyl group in $R^{11}$, $R^{12}$, $R^{13}$, $R^{14}$, $R^{15}$, $R^{16}$, $R^{17}$, $R^{18}$, $R^{19}$ and $R^{20}$ preferably has about 5 to 10 carbon atoms. Specific examples of the cycloalkyl group which may be substituted with at least one group selected from the group consisting of a hydroxyl group, an amino group which may be substituted with a C1-C4 alkyl group and a C1-C6 alkoxy group include a cyclopentyl group, a cyclohexyl group, a cycloheptyl group and a cyclooctyl group.

The aryl group in $R^{11}$, $R^{12}$, $R^{13}$, $R^{14}$, $R^{15}$, $R^{17}$, $R^{18}$, $R^{19}$ and $R^{20}$ preferably has about 6 to 10 carbon atoms. Specific examples of the aryl group which may be substituted with at least one group selected from the group consisting of a hydroxyl group, an amino group which may be substituted with a C1-C4 alkyl group and a C1-C6 alkoxy group include a phenyl group and a naphthyl group.

The alkoxy group in $R^{13}$, $R^{14}$ and $R^{15}$ preferably has about 1 to 6 carbon atoms and specific examples thereof include a methoxy group, an ethoxy group, an n-propoxy group, an isopropoxy group, an n-butoxy group, a tert-butoxy group, an n-pentyloxy group and an n-hexyloxy group.

The alkylene and alkenylene groups in W preferably have 2 to 6 carbon atoms. Specific examples of the alkylene group include an ethylene group, a trimethylene group, a tetramethylene group, a methylenedioxy group and an ethylene-1,2-dioxy group, and specific examples of the alkenylene group include an ethene-1,2-diyl group, a 1-propene-1,3-diyl group and a 2-butene-1,4-diyl group.

Specific examples of the amine compound include n-hexylamine, n-heptylamine, n-octylamine, n-nonylamine, n-decylamine, aniline, 2-methylaniline, 3-methylaniline, 4-methylaniline, 4-nitroaniline, 1-naphthylamine, 2-naphthylamine, ethylenediamine, tetramethylenediamine, hexamethylenediamine, 4,41-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, N,N-dimethylaniline, 2,6-diisopropylaniline, imidazole, benzimidazole, pyridine, 4-methylpyridine, 4-methylimidazole, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine and 3,3'-dipicolylamine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

A hindered amine compound having a piperidine skelton as disclosed in JP 11-52575 A1 can be also used as the quencher.

In the point of forming patterns having higher resolution, the quaternary ammonium hydroxide is preferably used as the quencher.

When the basic compound is used as the quencher, the present resist composition preferably includes 0.01 to 1% by weight of the basic compound based on the total amount of the resin component and the acid generator component.

The present resist composition can contain, if necessary, a small amount of various additives such as a sensitizer, a dissolution inhibitor, other polymers, a surfactant, a stabilizer and a dye as long as the effect of the present invention is not prevented.

The present resist composition is usually in the form of a resist liquid composition in which the above-mentioned ingredients are dissolved in a solvent and the resist liquid composition is applied onto a substrate such as a silicon wafer by a conventional process such as spin coating. The solvent used is sufficient to dissolve the above-mentioned ingredients, have an adequate drying rate, and give a uniform and smooth coat after evaporation of the solvent. Solvents generally used in the art can be used.

Examples of the solvent include a glycol ether ester such as ethyl cellosolve acetate, methyl cellosolve acetate and propylene glycol monomethyl ether acetate; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone. These solvents may be used alone and two or more thereof may be mixed to use.

A resist film applied onto the substrate and then dried is subjected to exposure for patterning, then heat-treated to facilitate a deblocking reaction, and thereafter developed with an alkali developer. The alkali developer used may be any one of various alkaline aqueous solution used in the art. Generally, an aqueous solution of tetramethylammonium hydroxide or (2-hydroxyethyl)trimethylammonium hydroxide (commonly known as "choline") is often used.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [HLC-8120GPC Type, Column (Three Columns): TSKgel Multipore HXL-M, Solvent: Tetrahydrofuran, manufactured by TOSOH CORPORATION] using styrene as a standard reference material. Structures of compounds were determined by NMR (GX-270 Type, or EX-270 Type, manufactured by JEOL LTD.) and mass spectrometry (Liquid Chromatography: 1100 Type, manufactured by AGILENT TECHNOLOGIES LTD., using Sumipax ODS-A210EC as column and water/acetonitrile as an eluent, Mass Spectrometry: LC/MSD Type or LC/MSD TOF Type, manufactured by AGILENT TECHNOLOGIES LTD.).

Example 1

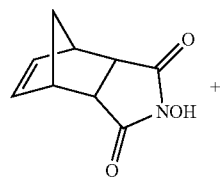

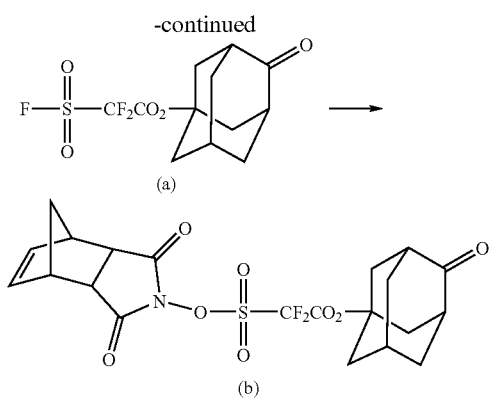

To the solution prepared by mixing 2.0 g of N-hydroxy-5-norbornene-2,3-dicarboximide with 4.4 g of N,N-dimethylformamide, 1.4 g of 2,6-lutidine and 4.0 g of the compound represented by the above-mentioned formula (a) was added. The resultant mixture was stirred for 24 hours at room temperature. To the obtained reaction mixture, a saturated aqueous ammonium chloride solution was added, and then the resultant mixture was extracted with ethylacetate. The obtained organic layer was washed with ion-exchanged water and then concentrated under reduced pressure. The obtained residue was purified with silica gel chromatography to obtain 2.4 g of the compound represented by the above-mentioned formula (b), which is called as B1.

$^1$H-NMR (dimethylsulfoxide-$d_6$): δ (ppm) 6.08 (2H, s), 3.53 (2H, dd, J=3.1 Hz, 1.5 Hz), 3.34 (2H, s), 2.57 (2H, s), 2.45-2.29 (7H, m), 2.02 (2H, d, J=12.2 Hz), 1.85 (2H, d, J=13.0 Hz), 1.60 (1H, d, J=9.2 Hz), 1.53 (1H, d, J=9.2 Hz)

$^{19}$F-NMR (dimethylsulfoxide-$d_6$): δ (ppm) −97.58

$^{13}$C-NMR (dimethylsulfoxide-$d_6$): δ (ppm) 213.07, 168.81, 154.25, 134.65, 112.16, 86.20, 50.81, 46.38, 44.44, 42.59, 39.70, 38.76, 37.00, 29.61

MS (ESI (+) Spectrum): [M+Na]$^+$ 508.1 ($C_{21}H_{21}F_2NO_8S^+$=485.10)

Example 2

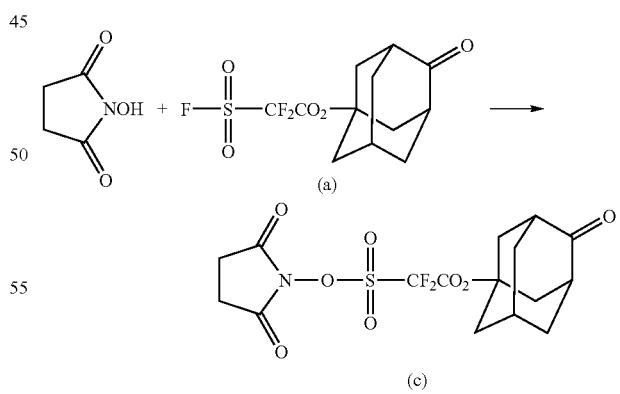

To the solution prepared by mixing 2.5 g of N-hydroxysuccinimide with 5.5 g of tetrahydrofuran, 1.4 g of 2,6-lutidine and 4.5 g of the compound represented by the above-mentioned formula (a) were added. The resultant mixture was stirred for 15 hours at room temperature. To the obtained reaction mixture, a saturated aqueous ammonium chloride solution was added, and then the resultant mixture was extracted with ethyl acetate. The obtained organic layer was washed with ion-exchanged water and then concentrated under reduced pressure. The obtained residue was purified with silica gel chromatography to obtain 2.3 g of the compound represented by the above-mentioned formula (c), which is called as B2.

$^1$H-NMR (dimethylsulfoxide-$d_6$): δ (ppm) 2.84 (4H, s), 2.59 (2H, s), 2.45-2.34 (7H, m), 2.03 (2H, d, J=12.2 Hz), 1.87 (2H, d, J=13.0 Hz)

$^{19}$F-NMR (dimethylsulfoxide-$d_6$): δ (ppm) −97.90

$^{13}$C-NMR (dimethylsulfoxide-$d_6$): δ (ppm) 213.11, 169.05, 154.29, 112.23, 86.19, 46.40, 39.73, 38.78, 37.02, 29.63, 25.40

MS (ESI (+) Spectrum): [M+Na]$^+$ 444.0 ($C_{16}H_{17}F_2NO_8S^+$=421.06)

Example 3

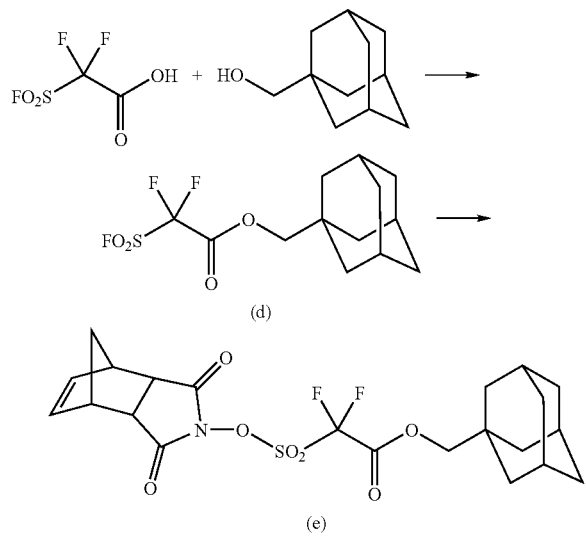

(1) To the solution prepared by mixing 5 g of difluoro(fluorosulfonyl)acetic acid with 15 g of dichloroethane, 5.6 g of adamantanemethanol and 0.1 g of sulfuric acid were added, and the resultant mixture was stirred for 3 hours under reflux. The obtained reaction mixture was cooled to room temperature, and 40 g of 10% aqueous sodium hydrogen carbonate solution was added thereto followed by extracting with 80 g of chloroform. The obtained organic layer was washed with water and then concentrated under reduced pressure to obtain 9.2 g of the compound represented by the above-mentioned formula (d). $^1$H-NMR (dimethylsulfoxide-$d_6$): δ (ppm) 4.10 (1.7H, s), 2.01-1.88 (3.0H, m), 1.75-1.44 (12.0H, m)

(2) To the solution prepared by mixing 4.3 g of N-hydroxy-5-norborne-2,3-dicarboximide with 18.9 g of N,N-dimethylformamide, 3.1 g of 2,6-lutidine and 8.5 g of the compound represented by the above-mentioned formula (d) were added. The resultant mixture was stirred for 17 hours at room temperature. To the obtained reaction mixture, a saturated aqueous ammonium chloride solution was added, and then the resultant mixture was extracted with ethyl acetate. The obtained organic layer was washed with ion-exchanged water and then concentrated under reduced pressure. The obtained residue was purified with silica gel chromatography to obtain 2.6 g of the compound represented by the above-mentioned formula (e), which is called as B3.

$^1$H-NMR (dimethylsulfoxide-$d_6$): δ (ppm) 6.10 (2H, s), 4.07 (2H, s), 3.55 (2H, dd, J=3.1 Hz, 1.5 Hz), 3.36 (2H, s), 1.95 (3H, s), 1.72-1.49 (14H, m)

$^{19}$F-NMR (dimethylsulfoxide-$d_6$); δ (ppm) −98.07

$^{13}$C-NMR (dimethylsulfoxide-$d_6$): δ (ppm) 168.82, 156.08, 134.66, 112.31, 77.94, 50.82, 44.49, 42.56, 37.82, 36.15, 33.07, 27.17

MS (ESI (+) Spectrum): [M+Na]$^+$ 508.1 ($C_{22}H_{21}F_2NO_7S^+$=485.10)

Example 4

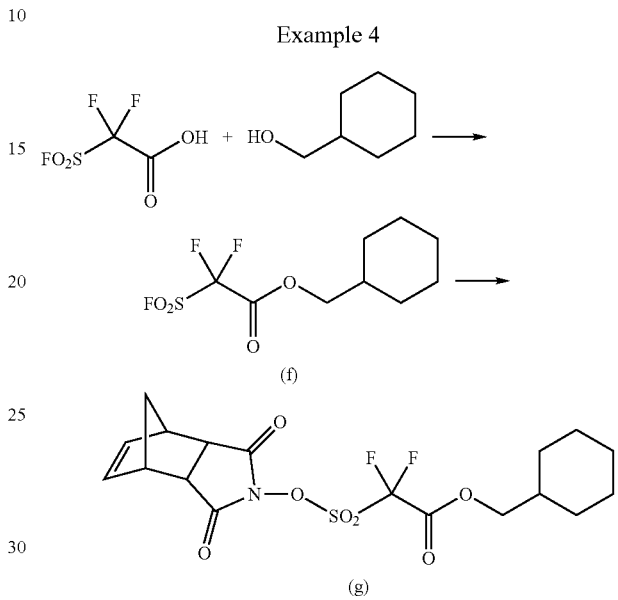

(1) To the solution prepared by mixing 7 g of difluoro(fluorosulfonyl)acetic acid with 21 g of dichloroethane, 5.4 g of cyclohexanemethanol and 0.02 g of sulfuric acid were added, and the resultant mixture was stirred for 6 hours under reflux. The obtained reaction mixture was cooled to room temperature, and 85 g of 10% aqueous sodium hydrogen carbonate solution was added thereto followed by extracting with 205 g of chloroform. The obtained organic layer was washed with water and then concentrated under reduced pressure to obtain 10.7 g of the compound represented by the above-mentioned formula (f).

$^1$H-NMR (dimethylsulfoxide-$d_6$): δ (ppm) 4.32 (2.0H, d, J=5.94 Hz), 1.78-1.55 (6.0H, m), 1.30-0.91 (5.0H, m)

(2) To the solution prepared by mixing 4.0 g of N-hydroxy-5-norbornene-2,3-dicarboximide with 17.6 g of N,N-dimethylformamide, 2.8 g of 2,6-lutidine and 5.9 g of the compound represented by the above-mentioned formula (f) were added. The resultant mixture was stirred for 17 hours at room temperature. To the obtained reaction mixture, a saturated aqueous ammonium chloride solution was added, and then the resultant mixture was extracted with ethylacetate. The obtained organic layer was washed with ion-exchanged water and then concentrated under reduced pressure. The obtained residue was purified with silica gel chromatography to obtain 1.3 g of the compound represented by the above-mentioned formula (g), which is called as B4.

$^1$H-NMR (dimethylsulfoxide-$d_6$): δ (ppm) 6.10 (2H, t, J=1.9 Hz), 4.28 (2H, d, J=6.1 Hz), 3.56-3.54 (2H, m), 3.37-3.34 (2H, m), 1.74-1.60 (7H, m), 1.54 (1H, d, J=9.2 Hz), 1.27-1.05 (3H, m), 1.05-0.95 (2H, m)

$^{19}$F-NMR (dimethylsulfoxide-$d_6$): δ (ppm) −98.05

$^{13}$C-NMR (dimethylsulfoxide-$d_6$): δ (ppm) 168.82, 156.05, 134.66, 112.36, 73.96, 50.82, 44.47, 42.59, 36.17, 28.32, 25.63, 24.95

MS (ESI (+) Spectrum): [M+Na]$^+$ 456.0 ($C_{18}H_{21}F_2NO_7$ S$^+$=433.10)

Example 5

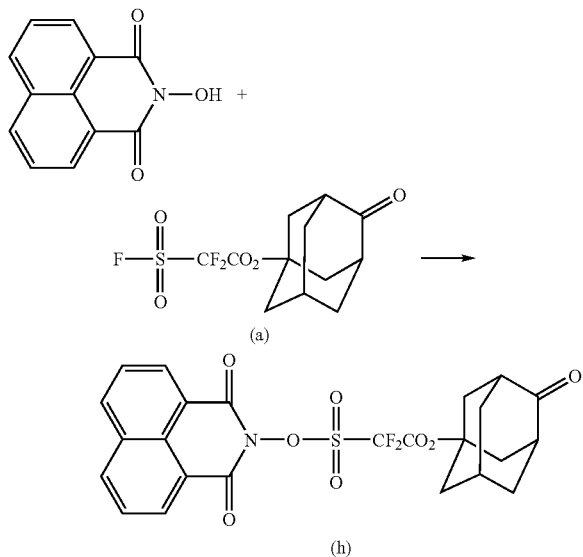

The mixture was prepared by mixing 2.2 g of N-hydroxy-1,8-naphthalimide, 2.1 g of potassium carbonate and 29 g of N,N-dimethylformamide. To the mixture, a solution prepared by mixing 3.3 g of the compound represented by the above-mentioned formula (a) with 6 g of N,N-dimethylformamide was added dropwise at room temperature. The resultant mixture was stirred for 3 hours at room temperature. The obtained reaction mixture was diluted with ion-exchanged water followed by extracting with chloroform. The obtained organic layer was washed with ion-exchanged water and then concentrated. The obtained residue was purified with silica gel chromatography to obtain 2.2 g of the compound represented by the above-mentioned formula (h), which is called as B5.

$^1$H-NMR (dimethylsulfoxide-d$_6$): δ (ppm) 8.63-8.58 (4H), 7.97-7.94 (2H), 2.60-2.38 (9H), 2.06-1.87 (4H)

$^{19}$F-NMR (dimethylsulfoxide-d$_6$): δ (ppm) −96.92

$^{13}$C-NMR (dimethylsulfoxide-d$_6$): δ (ppm) 213.24, 159.61, 154.81, 136.31, 132.36, 131.74, 127.73, 126.87, 121.42, 114.98-110.19 (t), 86.00, 46.57, 40.00, 39.00, 37.20

MS (ESI (+) Spectrum): [M+Na]$^+$ 542.0 ($C_{24}H_{19}F_2NO_8$ S$^+$=519.08)

Example 6

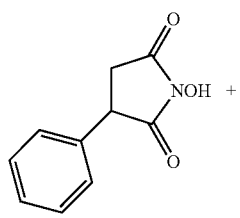

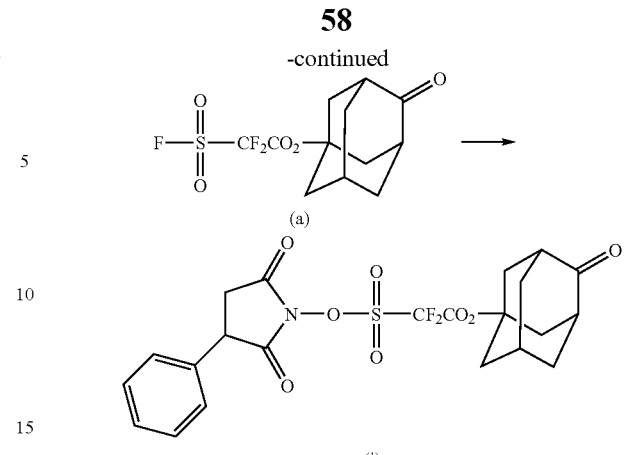

To the solution prepared by mixing 0.7 g of N-hydroxyphenylsuccinimide with 2.6 g of tetrahydrofuran, 0.4 g of 2,6-lutidine and 1.2 g of the compound represented by the above-mentioned formula (a) were added. The resultant mixture was stirred for 15 hours at room temperature. To the obtained reaction mixture, a saturated aqueous ammonium chloride solution was added, and then the resultant mixture was extracted with ethyl acetate. The obtained organic layer was washed with ion-exchanged water and then concentrated under reduced pressure. The obtained residue was purified with silica gel chromatography to obtain 0.3 g of the compound represented by the above-mentioned formula (I), which is called as B6.

$^1$H-NMR (dimethylsulfoxide-d$_6$): δ (ppm) 7.54-7.19 (5H, m), 4.40 (1H, dd, J=10.0 Hz, 5.0 Hz), 3.37 (1H, dd, J=18.0 Hz, 9.0 Hz), 3.05 (2H, dd, J=18.0 Hz, 5.4 Hz), 2.60-2.53 (2H, m), 2.40-2.31 (7H, m), 2.01 (2H, d, J=12.5 Hz), 1.84 (2H, d, J=12.9 Hz)

Example 7

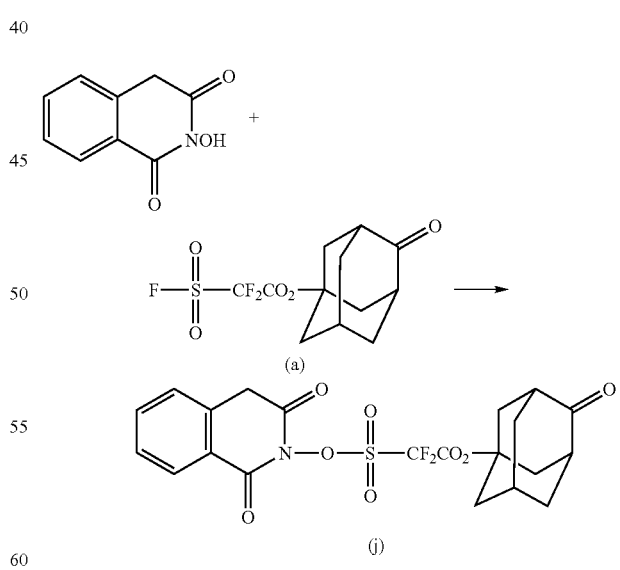

To the solution prepared by mixing 0.6 g of N-hydroxyhomophthalimide with 1.6 g of N,N-dimethylformamide, 0.3 g of 2,6-lutidine and 1.0 g of the compound represented by the above-mentioned formula (a) were added. The resultant mixture was stirred for 15 hours at room temperature. To the obtained reaction mixture, a saturated aqueous ammonium chloride solution was added, and then the resultant mixture was extracted with ethyl acetate. The obtained organic layer was washed with ion-exchanged water and then concentrated under reduced pressure. The obtained residue was purified with silica gel chromatography to obtain 0.3 g of the compound represented by the above-mentioned formula (j), which is called as B7.

¹H-NMR (dimethylsulfoxide-d₆): δ (ppm) 8.08-7.59 (4H, m), 4.12 (2H, d, J=5.6 Hz), 2.51-2.46 (2H, m), 2.41-2.31 (7H, m), 1.97 (2H, d, J=13.2 Hz), 1.83 (2H, d, J=9.6 Hz)

Example 8

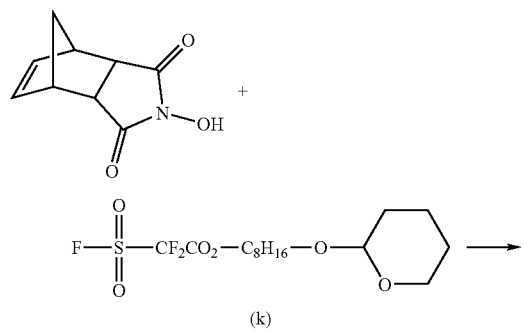

To the solution prepared by mixing 1.0 g of N-hydroxy-5-norborne-2,3-dicarboximide with 0.9 g of N,N-dimethylformamide, 0.7 g of 2,6-lutidine and 4.8 g of the compound represented by the above-mentioned formula (k) was added. The resultant mixture was stirred for 18 hours at room temperature. The obtained reaction mixture was purified with silica gel chromatography to obtain 1.2 g of the compound represented by the above-mentioned formula (I), which is called as B8.

¹H-NMR (dimethylsulfoxide-d₆): δ (ppm) 6.08 (2H, s), 4.53-4.49 (1H, m), 4.44 (2H, t, J=6.3 Hz), 3.76-3.65 (1H, m), 3.61-3.48 (3H, m), 3.46-3.14 (5H, m), 1.76-1.17 (20H, m)

Example 9

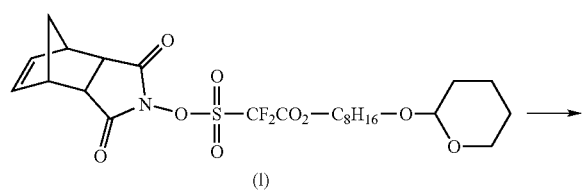

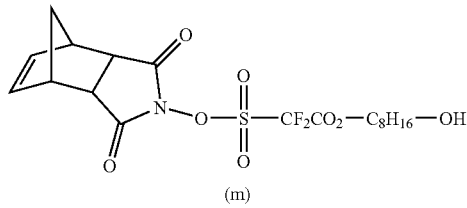

One point two grams of the compound represented by the above-mentioned formula (I) was dissolved in 2 g of methanol. To the obtained solution, 0.02 g of p-toluenesulfonic acid monohydrate was added, and the resultant mixture was stirred for 5 hours at room temperature. To the obtained reaction mixture, 10 g of methanol and 10 g of heptane were added and a methanol layer was separated. To the methanol layer, 3 g of ion-exchanged water was added and then extraction with ethyl acetate was conducted. The obtained organic layer was washed and concentrated under reduced pressure to obtain 0.8 g of the compound represented by the above-mentioned formula (m), which is called as B9.

¹H-NMR (dimethylsulfoxide-d₆) δ (ppm) 6.09 (2H, s), 4.43 (2H, t, J=6.4 Hz), 3.73-3.47 (3H, brm), 3.39-3.22 (4H, m), 1.56 (2H, dd, J=20.5 Hz, 8.9 Hz), 1.47-1.19 (12H, m)

Example 10

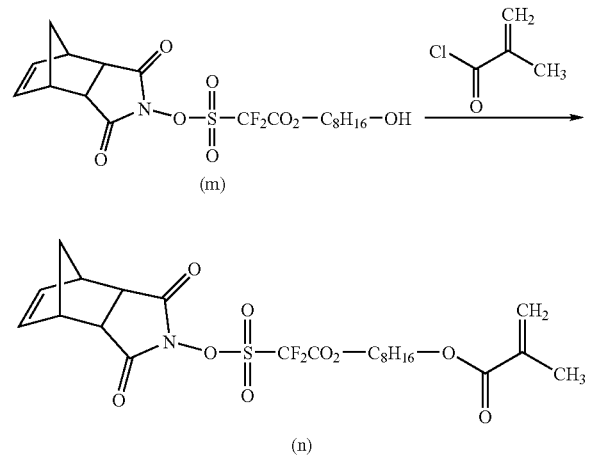

To the solution prepared by mixing 0.8 g of the compound represented by the above-mentioned formula (m) with 4 g of tetrahydrofuran, 0.3 g of 2,6-lutidine and 0.3 g of methacryloyl chloride was added. The resultant mixture was stirred for 1 hour at 0° C. The obtained reaction mixture was purified with silica gel chromatography to obtain 0.9 g of the compound represented by the above-mentioned formula (n), which is called as B10.

¹H-NMR (dimethylsulfoxide-d₆): δ (ppm) 6.08 (2H, s), 6.02-5.98 (1H, m), 5.65 (1H, t, J=1.6 Hz), 4.44 (2H, t, J=6.3 Hz), 4.07 (2H, t, J=6.6 Hz), 3.55-3.51 (2H, m), 3.30-3.25 (2H, m), 1.86 (3H, s), 1.65-1.20 (14H, m)

Example 11

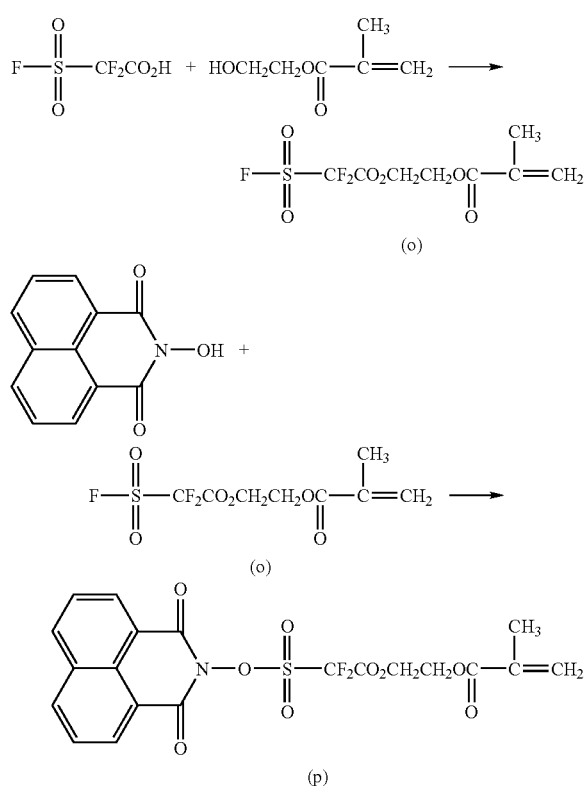

(1) Forty nine point three grams of difluoro(fluorosulfonyl) acetic acid and 30 g of 2-hydroxyethyl methacrylate were dissolved in 300 g of dichloroethane. To the obtained solution, a small amount of p-methoxyphenol was added as a polymerization inhibitor and then 0.45 g of concentrated sulfuric acid was added thereto. The resultant mixture was refluxed at 87° C. for 7 hours. The obtained reaction mixture was cooled to room temperature and 300 g of ion-exchanged water and 200 g of chloroform were added thereto followed by conducting extraction. The obtained organic layer was washed three times with pure water and then concentrated under reduced pressure to obtain 56.7 g of the compound represented by the above-mentioned formula (o). Yield: 84.8%.

$^1$H-NMR (dimethylsulfoxide-$d_6$): δ (ppm) 6.03 (1H, d, J=1.5 Hz), 5.73-5.70 (1H, m), 4.77 (2H, t, J=4.6 Hz), 4.43 (2H, t, J=4.6 Hz), 1.87 (3H, s)

$^{19}$F-NMR (dimethylsulfoxide-$d_6$): δ (ppm) −45.03, −99.46
MS: M$^+$ 291.0 ($C_8H_9F_3O_6S^+$=290.01)

(2) Fourteen point seven grams of N-hydroxy-1,8-naphthalimide and 14.3 g of potassium carbonate were dissolved in 180 g of N,N-dimethylformamide. To the obtained solution, 20.0 g of the compound represented by the above-mentioned formula (o) was added, and then a small amount of pyridine and a small amount of p-methoxyphenol as a polymerization inhibitor were also added thereto. The resultant mixture was stirred for 2 hours at 28 to 30° C. The obtained reaction mixture was filtrated to separate the insoluble matters. The insoluble matters were washed with 300 g of chloroform. The filtrate was diluted with 500 g of 1% aqueous oxalic acid solution and 300 g of chloroform to conduct extraction. The obtained organic layer was washed with ion-exchanged water and then concentrated to obtain 22.7 g of the compound represented by the above-mentioned formula (p), which is called as B11. Yield: 68.1%.

$^1$H-NMR (dimethylsulfoxide-$d_6$): δ (ppm) 8.60 (2H, d, J=7.7 Hz), 8.30 (2H, d, J=8.5 Hz), 7.80(2H, t, J=7.7 Hz), 6.11(1H, s), 5.53 (1H, s), 4.79 (2H, m), 4.52 (2H, m), 1.88 (3H, s)

$^{19}$F-NMR (dimethylsulfoxide-$d_6$): δ (ppm) −96.44
$^{13}$C-NMR (dimethylsulfoxide-$d_6$) δ (ppm) 166.75, 159.02, 157.04, 135.75, 132.58, 131.73, 127.23, 127.02, 126.44, 125.82, 121.28, 115.30-110.51 (t), 66.24, 61.26, 18.04

MS (ESI (+) Spectrum): [M+Na]$^+$ 506.0 ($C_{20}H_{15}F_2NO_9S$=483.04)

Monomers used in the following Examples are following monomers M1, M2 and M3.

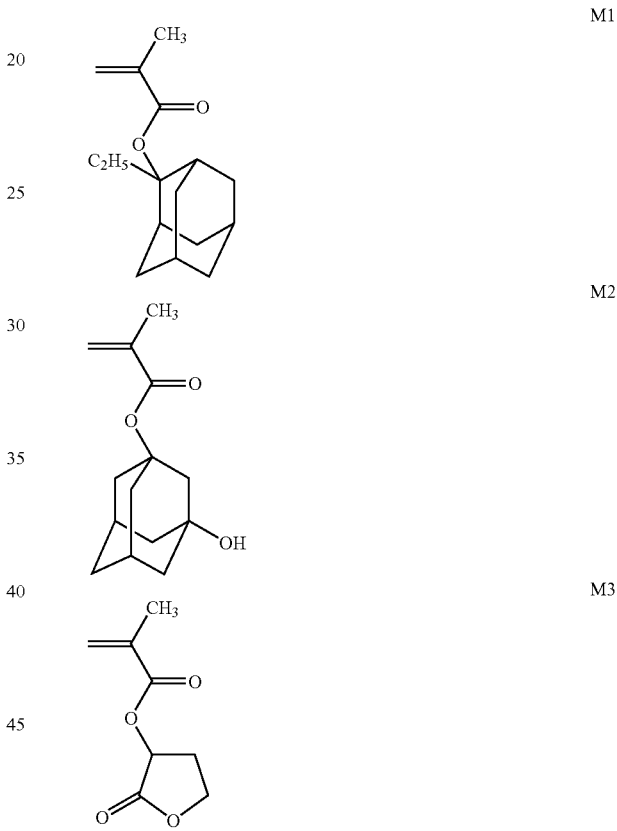

Example 12

The solution was prepared by mixing 12.3 g of monomer M1, 5.90 g of monomer M2, 4.25 g of monomer M3, 4.8 g of B11, 0.7 g of 2,2'-azobisisobutyronitrile and 45 g of 1,4-dioxane. To a four-necked flask, 10 g of 1,4-dioxane was added, and then heated to 70° C. The above solution was added dropwise thereto over 2 hours at 72 to 75° C. The resultant mixture was heated at 72 to 75° C. for 5 hours. The reaction mixture was cooled and then pored into 90% aqueous methanol solution to cause precipitation. The precipitate was isolated, washed with methanol and then dried at 40° C. under reduced pressure to obtain 21.2 g of a polymer having a weight-average molecular weight of 17,808 and a degree of dispersion (Mw/Mn) of 2.245 in a yield of 77.9%. This polymer had the following structural units. This is called as B12.

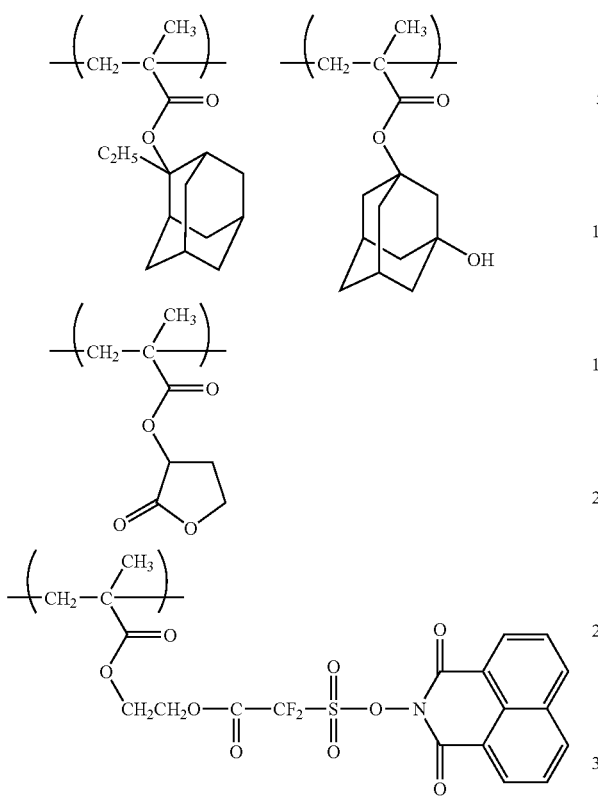

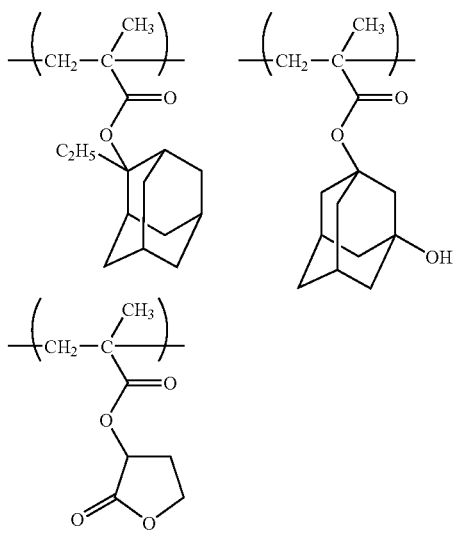

Examples 13 to 14 and Comparative Example 1

<Acid generator>

B1, B2
C1:

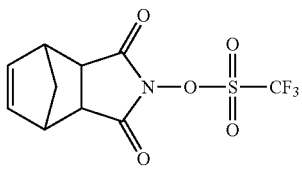

Herein, the weight-average molecular weight of B12 was measured by gel permeation chromatography analysis [Apparatus: HLC-8120GPC Type, Column: TSK-GELG2000HXL and TSK-GELG4000HXL, which were connected in series, Solvent: tetrahydrofuran, manufactured by TOSOH CORPORATION] using polystyrene as a standard reference material.

<Quencher>

Q1: 2,6-diisopropylaniline

<Solvent>

| Y1: | propylene glycol monomethyl ether acetate | 100 parts |
| | 2-heptanone | 20 parts |
| | propylene glycol monomethyl ether | 40 parts |
| | γ-butyrolactone | 3.5 parts |

Resin Synthetic Example 1

Monomer M1, monomer M2 and monomer M3 were dissolved in 2 times amount of methyl isobutyl ketone as much as the amount of all monomers to be used (monomer molar ratio; monomer M1: monomer M2: monomer M3-5:2.5:2.5). To the solution, 2,2'-azobisisobutyronitrile was added as an initiator in a ratio of 2 mol % based on all monomer molar amount, and the resultant mixture was heated at 80° C. for about 8 hours. The reaction solution was poured into a large amount of heptane to cause precipitation. The precipitate was isolated and dissolved in methyl isobutyl ketone. The obtained solution was poured into a large amount of heptane to cause precipitation. The precipitate was isolated and dissolved in methyl isobutyl ketone. The obtained solution was poured into a large amount of heptane to cause precipitation. The precipitate was isolated and dissolved in methyl isobutyl ketone. The obtained solution was poured into a large amount of heptane to cause precipitation. The precipitate was isolated. As a result, a copolymer having a weight-average molecular weight of about 9,200 was obtained. This copolymer had the following structural units. This is called as resin A1.

The following components were mixed and dissolved, further, filtrated through a fluorine resin filter having pore diameter of 0.2 μm, to prepare resist compositions.

Resin (kind and amount are described in Table 1)
Acid generator (kind and amount are described in Table 1)
Quencher (kind and amount are described in Table 1)
Solvent (kind is described in Table 1)

TABLE 1

| Ex. No. | Resin (kind/amount (part)) | Acid generator (kind/amount (part)) | Quencher (kind/amount (part)) | Solvent |
|---|---|---|---|---|
| Ex. 13 | A1/10 | B1/2.00 | Q1/0.025 | Y1 |
| Ex. 14 | A1/10 | B2/1.74 | Q1/0.025 | Y1 |
| Comp. Ex. 1 | A1/10 | C1/1.28 | Q1/0.025 | Y1 |

Silicon wafers were each coated with "ARC-29A-8", which is an organic anti-reflective coating composition available from Nissan Chemical Industries, Ltd., and then baked at 205° C. for 60 seconds, to form a 780 Å-thick organic anti-reflective coating. Each of the resist compositions prepared as above was spin-coated over the anti-reflective coating so that the thickness of the resulting film became 0.15 μm after drying. The silicon wafers thus coated with the respective resist liquids were each prebaked on a proximity hotplate at 105° C. for 60 seconds. Using an ArF excimer stepper ("FPA-5000AS3" manufactured by CANON INC., NA=0.75, 2/3 Annular), each wafer thus formed with the respective resist film was subjected to line and space pattern exposure, with the exposure quantity being varied stepwise.

After the exposure, each wafer was subjected to post-exposure baking on a hotplate at 105° C. for 60 seconds and then to paddle development for 15 seconds with an aqueous, solution of 2.38 wt % tetramethylammonium hydroxide.

Each of a dark field pattern developed on the organic anti-reflective coating substrate after the development was observed with a scanning electron microscope ("S4100", manufactured by Hitachi, Ltd.). The results thereof are shown in Table 2. The term "dark field pattern", as used herein, means a pattern obtained by exposure and development through a reticle comprising chromium base surface (light-shielding portion) and linear glass layers (light-transmitting portion) formed in the chromium surface and aligned with each other. Thus, the dark field pattern is such that, after exposure and development, resist layer surrounding the line and space pattern remains on substrate.

Resolution: It is expressed as the minimum size of space pattern which gave the space pattern split by the line pattern at the exposure amount of the effective sensitivity.

Pattern Profile: Each of patterns developed on the organic anti-reflective coating substrate after the development, which was obtained at the amount of exposure of effective sensitivity. When the cross-section shape of the pattern is rectangle, the pattern profile is good and its evaluation is marked by "○", and when the cross-section shape of the pattern is taper shape, the pattern profile is bad and its evaluation is marked by "X".

TABLE 2

| Ex. No. | Resolution (μm) | Pattern Profile |
|---|---|---|
| Ex. 13 | 0.10 | ○ |
| Ex. 14 | 0.095 | ○ |
| Comp. Ex. 1 | 0.12 | X |

Example 15 and Comparative Examples 2 and 3

According to the same manner described in Example 13, the resist composition containing B1 was prepared, which composition is called as R1. According to the same manner described in Example 13, the resist composition containing triphenylsulfonium trifluoromethanesulfonate was prepared, which composition is called as R2. According to the same manner described in Comparative Example 1, the resist composition containing C1 was prepared, which composition is called as R3.

The leaching property of the acid generator was measured as followed;
Silicon wafer was coated with the resist composition. O-ring having a diameter of 52.8 mm was put on the resist film. Onto the resist film in the o-ring, 20 μL of pure water was poured using a microsyringe. After 10 seconds, the water sample was collected using a microsyringe and analyzed according to the following condition to measure a concentration of an anion containing the collected water sample. The results are shown in Table 3.

<Analytical Condition>
Apparatus: Liquid chromatography apparatus (1100 Type) manufactured by AGILENT TECHNOLOGIES LTD., and Mass Spectrometer (LC/MSD TOF Type) manufactured by AGILENT TECHNOLOGIES LTD. Column: SUMIPAX ODS A-210MS (5 μm×2.0 mm φ×150 mm)
Eluent: A: 0.05% aqueous trifluoroacetic acid solution
B: 0.05% trifluoroacetic acid/acetonitrile solution
A/B=90/10 (0 to 1 min.) to 0/100 (16 min.)
Flow rate: 0.3 mL/min.
Injection Volume: 100 μL
Detector: UV-VIS 210, 220, 254 nm
Ionization: ESI$^{+,-}$
VCap: 4500 V
Mass Range: 50 to 500
Transients: 20,000
Fragmentor=Pos: 215 V
Neg: 175 V
Skimmer: 60 V
Drying Gas: 350° C., 13.0 L/min.
Neb pres: 35 psi

TABLE 3

| Ex. No. | Acid Generator | Resist Composition | Anion Concentration (mol/cm$^3$) |
|---|---|---|---|
| Ex. 15 | B1 | R1 | $3 \times 10^{-13}$ |
| Comp. Ex. 2 | triphenylsulfonium trifluoromethanesulfonate | R2 | $5 \times 10^{-12}$ |
| Comp. Ex. 3 | C1 | R3 | $5 \times 10^{-12}$ |

The present imide compound has better leaching property.

Example 16

The resist composition is prepared according to the same manner as that of Example 13, except that B3 is used as an acid generator in place of BE. The pattern is obtained according to the same manner as that of Example 13, except that the resist composition containing B3 is used in place of the resist composition containing B1.

Example 17

The resist composition is prepared according to the same manner as that of Example 13, except that B4 is used as an acid generator in place of B1. The pattern is obtained according to the same manner as that of Example 13, except that the resist composition containing B4 is used in place of the resist composition containing B1.

Example 18

The resist composition is prepared according to the same manner as that of Example 13, except that B5 is used as an acid generator in place of B1. The pattern is obtained according to the same manner as that of Example 13, except that the resist composition containing B5 is used in place of the resist composition containing B1.

Example 19

The resist composition is prepared according to the same manner as that of Example 13, except that B6 is used as an acid generator in place of B1. The pattern is obtained according to the same manner as that of Example 13, except that the resist composition containing B6 is used in place of the resist composition containing B1.

Example 20

The resist composition is prepared according to the same manner as that of Example 13, except that B7 is used as an acid generator in place of B1. The pattern is obtained according to the same manner as that of Example 13, except that the resist composition containing B7 is used in place of the resist composition containing B1.

Example 21

The resist composition is prepared according to the same manner as that of Example 13, except that B8 is used as an acid generator in place of B1. The pattern is obtained according to the same manner as that of Example 13, except that the resist composition containing B8 is used in place of the resist composition containing B1.

Example 22

The resist composition is prepared according to the same manner as that of Example 13, except that B9 is used as an acid generator in place of B1. The pattern is obtained according to the same manner as that of Example 13, except that the resist composition containing B9 is used in place of the resist composition containing B1.

Example 23 and Comparative Example 4

<Resin>

B12, A1
<Acid generator>

C1
<Quencher>

Q1: 2,6-diisopropylaniline
<Solvent>

| Y2: | propylene glycol monomethyl ether acetate | 90 parts |
| | propylene glycol monomethyl ether | 130 parts |
| | γ-butyrolactone | 5.0 parts |

The following components Were mixed and dissolved, further, filtrated through a fluorine resin filter having pore diameter of 0.2 μm, to prepare resist compositions.
Resin (kind and amount are described in Table 4)
Acid generator (kind and amount are described in Table 4)
Quencher (kind and amount are described in Table 4)
Solvent (kind is described in Table 4)

TABLE 4

| Ex. No. | Resin (kind/amount (part)) | Acid generator (kind/amount (part)) | Quencher (kind/amount (part)) | Solvent |
|---|---|---|---|---|
| Ex. 23 | B12/10 | C1/0.50 | Q1/0.025 | Y2 |
| Comp. Ex. 4 | A1/10 | C1/1.28 | Q1/0.025 | Y2 |

Silicon wafers were each coated with "ARC-29A-B", which is an organic anti-reflective coating composition available from Nissan Chemical Industries, Ltd., and then baked at 205° C. for 60 seconds, to form a 780 Å-thick organic anti-reflective coating. Each of the resist compositions prepared as above was spin-coated over the anti-reflective coating so that the thickness of the resulting film became 0.15 μm after drying. The silicon wafers thus coated with the respective resist liquids were each prebaked on a proximity hotplate at 105° C. for 60 seconds. Using an ArF excimer stepper ("FPA-5000AS3" manufactured by CANON INC., NA=0.75, 2/3 Annular), each wafer thus formed with the respective resist film was subjected to line and space pattern exposure, with the exposure quantity being varied stepwise.

After the exposure, each wafer was subjected to post-exposure baking on a hotplate at 105° C. for 60 seconds and then to paddle development for 15 seconds with an aqueous solution of 2.38 wt % tetramethylammonium hydroxide.

Each of a dark field pattern developed on the organic anti-reflective coating substrate after the development was observed with a scanning electron microscope ("S4100", manufactured by Hitachi, Ltd.). The results thereof are shown in Table 5. The term "dark field pattern", as used herein, means a pattern obtained by exposure and development through a reticle comprising chromium base surface (light-shielding portion) and linear glass layers (light-transmitting portion) formed in the chromium surface and aligned with each other. Thus, the dark field pattern is such that, after exposure and development, resist layer surrounding the line and space pattern remains on substrate.

Pattern Profile: Each of patterns developed on the organic anti-reflective coating substrate after the development, which was obtained at the amount of exposure of effective sensitivity. When the upper surface or side wall surface of the pattern is smoother than that of Comparative Example 4, the pattern profile is good and its evaluation is marked by "○", when the upper surface or side wall surface of the pattern is similar to that of Comparative Example 4, the pattern profile is normal and its evaluation is marked by "Δ", and when the upper surface or side wall surface of the pattern is rougher than that of Comparative Example 4, the pattern profile is bad and its evaluation is marked by "X".

TABLE 5

| Ex. No. | Pattern Profile |
|---|---|
| Ex. 23 | ○ |
| Comp. Ex. 4 | — |

The present imide compound and the present polymer are novel and are useful as an acid generator, and the present composition containing the present imide compound or the present polymer provides a resist pattern having good pattern profile and is especially suitable for ArF excimer laser lithography, KrF excimer laser lithography and ArF immersion lithography.

What is claimed is:
1. An imide compound represented by the formula (I):

wherein $R^1$ represents a C1-C20 aliphatic hydrocarbon group, a C5-C10 aryl group or a C6-C20 aralkyl group, and the C1-C20 aliphatic hydrocarbon group, the C5-C10 aryl group and the C6-C20 aralkyl group may have one or more substituents and one or more heteroatoms, $W^1$ represents —CO—O—, —O—CO—, —CH$_2$O—, —O—CH$_2$—, —CH$_2$O—CO— or —CO—OCH$_2$—, $Q^1$ and $Q^2$ each independently represent a fluorine atom, a C1-C6 alkyl group or a C1-C6 perfluoroalkyl group, and A represents a group represented by the formula (I-1):

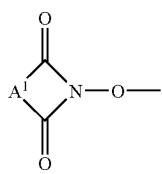
(I-1)

wherein $A^1$ represents —CH$_2$—CH$_2$—, —CH$_2$—CH$_2$—CH$_2$—, —CH=CH— or —CH=CH—CH$_2$—, in which one or more hydrogen atoms may be substituted with a C1-C6 aliphatic hydrocarbon group, a C3-C12 alicyclic hydrocarbon group or a C6-C10 aromatic hydrocarbon group, and the neighboring substituents may be bonded each other to form a ring, and the C1-C6 aliphatic hydrocarbon group, the C3-C12 alicyclic hydrocarbon group and the C6-C10 aromatic hydrocarbon group may have one or more substituents and one or more heteroatoms.

2. The imide compound according to claim 1, wherein $Q^1$ and $Q^2$ each independently represents a fluorine atom or a trifluoromethyl group.

3. The imide compound according to claim 1, wherein $Q^1$ and $Q^2$ are fluorine atoms.

4. The imide compound according to claim 1, wherein $R^1$ is a C1-C20 alkyl group substituted with an acryloyloxy group or a methacryloyloxy group and the C1-C20 alkyl group may have one or more substituents and one or more heteroatoms.

5. The imide compound according to claim 1, wherein $R^1$ is a C3-C20 alicyclic hydrocarbon group which may have one or more substituents and one or more heteroatoms.

6. The imide compound according to claim 1, wherein the compound represented by the formula (I) is a compound represented by the formula (III), (IV), (V), (VI) or (VII):

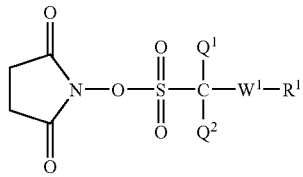
(III)

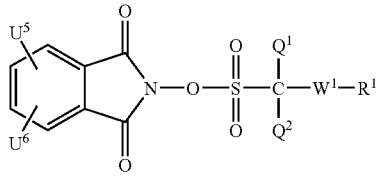
(IV)

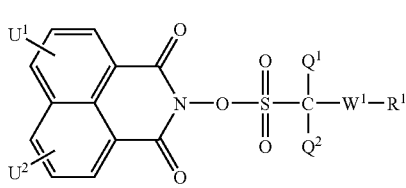
(V)

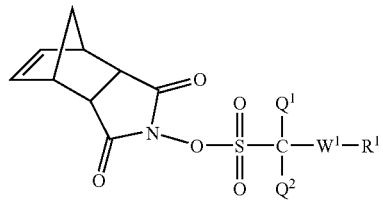
(VII)

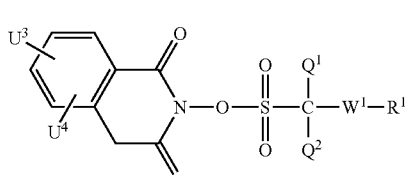
(VI)

wherein $U^1$ to $U^6$ each independently represent a hydrogen atom, a C1-C4 hydrocarbon group or a C1-C4 alkoxy group, and $R^1$, $W^1$, $Q^1$ and $Q^2$ are the same meanings as defined above.

7. A polymer comprising a structural unit derived from an imide compound according to claim 4.

8. The polymer according to claim 7, wherein the polymer contains a structural unit having an acid-labile group in addition to the structural unit derived from an imide compound according to claim 4.

9. A chemically amplified resist composition comprising a resin and an imide compound according to claim 1.

10. A chemically amplified resist composition comprising a resin and a polymer according to claim 7.

11. The chemically amplified resist composition according to claim 9 or 10, wherein the resin is a resin comprising a structural unit having an acid-labile group and being insoluble or poorly soluble in an aqueous alkali solution but becoming soluble in an aqueous alkali solution by the action of an acid.

12. The chemically amplified resist composition according to claim 9 or 10, wherein the resin further contains the other acid generator.

13. A process for producing an imide compound represented by the formula (I):

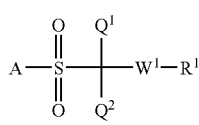
(I)

wherein $R^1$ represents a C1-C20 aliphatic hydrocarbon group, a C5-C10 aryl group or a C6-C20 aralkyl group, and the C1-C20 aliphatic hydrocarbon group, the C5-C10 aryl group and the C6-C20 aralkyl group may have one or more substituents and one or more heteroatoms, $W^1$ represents —CO—O—, —O—CO—, —CH$_2$O—, —O—CH$_2$—, —CH$_2$O—CO— or —CO—OCH$_2$—, $Q^1$ and $Q^2$ each independently represent, a fluorine atom, a C1-C6 alkyl group or a C1-C6 perfluoroalkyl group, and A represents a group represented by the formula (I-1):

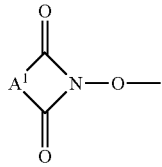

(I-1)

wherein $A^1$ represents —CH$_2$—CH$_2$—, —CH$_2$—CH$_2$—CH$_2$—, —CH=CH— or —CH=CH—CH$_2$—, in which one or more hydrogen atoms may be substituted with a C1-C6 aliphatic hydrocarbon group, a C3-C12 alicyclic hydrocarbon group or a C6-C10 aromatic hydrocarbon group, and the neighboring substituents may be bonded each other to form a ring, and the C1-C6 aliphatic hydrocarbon group, the C3-C12 alicyclic hydrocarbon group and the C6-C10 aromatic hydrocarbon group may have one or more substituents and one or more heteroatoms, which comprises reacting a compound represented by the formula (VIII):

A-H (VIII)

wherein A is the same as defined above, with a compound represented by the formula (IX):

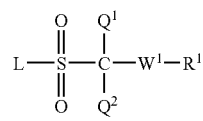

(IX)

wherein $R^1$, $W^1$, $Q^1$ and $Q^2$ are the same meanings as defined above, and L represents a halogen atom, in the presence of a base.

* * * * *